United States Patent
Nolte et al.

(10) Patent No.: US 7,787,126 B2
(45) Date of Patent: Aug. 31, 2010

(54) METHOD AND APPARATUS FOR CONJUGATE QUADRATURE INTERFEROMETRIC DETECTION OF AN IMMUNOASSAY

(75) Inventors: David D. Nolte, Lafayette, IN (US); Xuefeng Wang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 110 days.

(21) Appl. No.: 12/079,352

(22) Filed: Mar. 26, 2008

(65) Prior Publication Data

US 2008/0304073 A1    Dec. 11, 2008

Related U.S. Application Data

(60) Provisional application No. 60/896,979, filed on Mar. 26, 2007.

(51) Int. Cl.
*G01B 9/02* (2006.01)
(52) U.S. Cl. ...................................... 356/450
(58) Field of Classification Search ................. 356/450
See application file for complete search history.

(56) References Cited

U.S. PATENT DOCUMENTS

| | | | |
|---|---|---|---|
| 3,796,495 A | 3/1974 | Laub | |
| 4,537,861 A | 8/1985 | Elings et al. | |
| 4,649,529 A | 3/1987 | Avicola | |
| 4,741,620 A | 5/1988 | Wickramasinghe | |
| 4,876,208 A | 10/1989 | Gustafson et al. | |
| 4,899,195 A | 2/1990 | Gotoh | |
| 4,975,237 A | 12/1990 | Brown | |
| RE33,581 E | 4/1991 | Nicoli et al. | |
| 5,122,284 A | 6/1992 | Braynin et al. | |
| 5,155,549 A | 10/1992 | Dhadwal | |

(Continued)

FOREIGN PATENT DOCUMENTS

EP    1189062 A1    3/2002

(Continued)

OTHER PUBLICATIONS

Abe, Takao, et al., Microroughness Measurements on Polished Silicon Wafers, Jpn. 31, pp. 721-728, 1992.

(Continued)

*Primary Examiner*—Michael A Lyons
(74) *Attorney, Agent, or Firm*—Taft, Stettinius & Hollister, LLP

(57) ABSTRACT

A detection system for detecting target material is provided. The system comprises a photonic structure having a reflectance-band and associated side bands; an illumination source for illuminating at a wavelength in at least one of an edge of the reflectance-band and the side bands of the photonic structure and for generating a return beam; a detector system having an intensity-sensitive channel configured to detect an in-line signal from the return beam and a phase-sensitive channel configured to detect a differential phase contrast signal from the return beam; and a processing system for receiving and adding in quadrature the in-line signal and the differential phase contrast signal to generate a joint signal, and for determining one of the presence or the absence of the target material on the photonic structure using the joint signal.

10 Claims, 19 Drawing Sheets
(16 of 19 Drawing Sheet(s) Filed in Color)

U.S. PATENT DOCUMENTS

| | | | |
|---|---|---|---|
| 5,413,939 A | 5/1995 | Gustafson et al. | |
| 5,478,527 A | 12/1995 | Gustafson et al. | |
| 5,478,750 A | 12/1995 | Bernstein et al. | |
| 5,491,550 A | 2/1996 | Dabbs | |
| 5,494,829 A | 2/1996 | Sandstrom et al. | |
| 5,497,007 A | 3/1996 | Uritsky et al. | |
| 5,545,531 A | 8/1996 | Rava et al. | |
| 5,581,345 A | 12/1996 | Oki et al. | |
| 5,602,377 A | 2/1997 | Beller et al. | |
| 5,621,532 A | 4/1997 | Ooki et al. | |
| 5,629,044 A | 5/1997 | Rubenchik | |
| 5,631,171 A | 5/1997 | Sandstrom et al. | |
| 5,653,939 A | 8/1997 | Hollis et al. | |
| 5,700,046 A | 12/1997 | Van Doren et al. | |
| 5,717,778 A | 2/1998 | Chu et al. | |
| 5,736,257 A | 4/1998 | Conrad et al. | |
| 5,781,649 A | 7/1998 | Brezoczky | |
| 5,786,226 A | 7/1998 | Bocker et al. | |
| 5,837,475 A | 11/1998 | Dorsel et al. | |
| 5,843,767 A | 12/1998 | Beattie | |
| 5,844,871 A | 12/1998 | Maezawa | |
| 5,874,219 A | 2/1999 | Rava et al. | |
| 5,875,029 A | 2/1999 | Jann et al. | |
| 5,883,717 A | 3/1999 | DiMarzio et al. | |
| 5,892,577 A | 4/1999 | Gordon | |
| 5,900,935 A | 5/1999 | Klein et al. | |
| 5,922,617 A | 7/1999 | Wang et al. | |
| 5,935,785 A | 8/1999 | Reber et al. | |
| 5,945,334 A | 8/1999 | Besemer et al. | |
| 5,955,377 A | 9/1999 | Maul et al. | |
| 5,968,728 A | 10/1999 | Perttunen et al. | |
| 5,999,262 A | 12/1999 | Dobschal et al. | |
| 6,008,892 A | 12/1999 | Kain et al. | |
| 6,030,581 A | 2/2000 | Virtanen | |
| 6,048,692 A | 4/2000 | Maracas et al. | |
| 6,060,237 A | 5/2000 | Nygren et al. | |
| 6,071,748 A | 6/2000 | Modlin et al. | |
| 6,099,803 A | 8/2000 | Ackley | |
| 6,110,748 A | 8/2000 | Reber et al. | |
| 6,121,048 A | 9/2000 | Zaffaroni et al. | |
| 6,140,044 A | 10/2000 | Besemer et al. | |
| 6,143,247 A | 11/2000 | Sheppard | |
| 6,177,990 B1 | 1/2001 | Kain et al. | |
| 6,221,579 B1 | 4/2001 | Everhart et al. | |
| 6,238,869 B1 | 5/2001 | Kris et al. | |
| 6,248,539 B1 | 6/2001 | Ghadiri et al. | |
| 6,249,593 B1 | 6/2001 | Chu et al. | |
| 6,256,088 B1 | 7/2001 | Gordon | |
| 6,271,924 B1 | 8/2001 | Ngoi et al. | |
| 6,287,783 B1 | 9/2001 | Maynard et al. | |
| 6,287,850 B1 | 9/2001 | Besemer et al. | |
| 6,312,901 B2 | 11/2001 | Virtanen | |
| 6,312,961 B1 | 11/2001 | Voirin et al. | |
| 6,319,468 B1 | 11/2001 | Sheppard, Jr. et al. | |
| 6,319,469 B1 | 11/2001 | Mian et al. | |
| 6,320,665 B1 | 11/2001 | Ngoi et al. | |
| 6,327,031 B1 | 12/2001 | Gordon | |
| 6,339,473 B1 | 1/2002 | Gordon | |
| 6,342,349 B1 | 1/2002 | Virtanen | |
| 6,342,395 B1 | 1/2002 | Hammock et al. | |
| 6,345,115 B1 | 2/2002 | Ramm et al. | |
| 6,350,413 B1 | 2/2002 | Reichert et al. | |
| 6,355,429 B1 | 3/2002 | Nygren et al. | |
| 6,368,795 B1 | 4/2002 | Hefti | |
| 6,376,258 B2 | 4/2002 | Hefti | |
| 6,381,025 B1 | 4/2002 | Bornhop et al. | |
| 6,387,331 B1 | 5/2002 | Hunter | |
| 6,395,558 B1 | 5/2002 | Duveneck et al. | |
| 6,395,562 B1 | 5/2002 | Hammock et al. | |
| 6,399,365 B2 | 6/2002 | Besemer et al. | |
| 6,403,957 B1 | 6/2002 | Fodor et al. | |
| 6,416,642 B1 | 7/2002 | Alajoki et al. | |
| 6,469,787 B1 | 10/2002 | Meyer et al. | |
| 6,476,907 B1 | 11/2002 | Gordon | |
| 6,483,582 B2 * | 11/2002 | Modlin et al. | 356/317 |
| 6,483,585 B1 | 11/2002 | Yang | |
| 6,483,588 B1 | 11/2002 | Graefe et al. | |
| 6,496,267 B1 | 12/2002 | Takaoka | |
| 6,496,309 B1 | 12/2002 | Bliton et al. | |
| 6,540,618 B1 | 1/2003 | Morath et al. | |
| 6,518,056 B2 | 2/2003 | Schembri et al. | |
| 6,551,817 B2 | 4/2003 | Besemer et al. | |
| 6,566,069 B2 | 5/2003 | Virtanen | |
| 6,584,217 B1 | 6/2003 | Lawless et al. | |
| 6,591,196 B1 | 7/2003 | Yakhini et al. | |
| 6,596,483 B1 | 7/2003 | Choong et al. | |
| 6,602,702 B1 | 8/2003 | McDevitt et al. | |
| 6,623,696 B1 | 9/2003 | Kim et al. | |
| 6,624,896 B1 | 9/2003 | Neal et al. | |
| 6,649,403 B1 | 11/2003 | McDevitt | |
| 6,653,152 B2 | 11/2003 | Challener | |
| 6,656,428 B1 | 12/2003 | Clark et al. | |
| 6,685,885 B2 | 2/2004 | Nolte et al. | |
| 6,687,008 B1 | 2/2004 | Peale et al. | |
| 6,709,869 B2 | 3/2004 | Mian et al. | |
| 6,720,177 B2 | 4/2004 | Ghadiri et al. | |
| 6,733,977 B2 | 5/2004 | Besemer et al. | |
| 6,734,000 B2 | 5/2004 | Bhatia | |
| 6,737,238 B2 | 5/2004 | Suzuki | |
| 6,743,633 B1 | 6/2004 | Hunter | |
| 6,760,298 B2 | 7/2004 | Worthington et al. | |
| 6,766,817 B2 | 7/2004 | da Silva | |
| 6,770,447 B2 | 8/2004 | Maynard et al. | |
| 6,783,938 B2 | 8/2004 | Nygren et al. | |
| 6,787,110 B2 | 9/2004 | Tiefenthaler | |
| 6,791,677 B2 | 9/2004 | Kawai et al. | |
| 6,803,999 B1 | 10/2004 | Gordon | |
| 6,806,963 B1 | 10/2004 | Walti et al. | |
| 6,819,432 B2 | 11/2004 | Pepper et al. | |
| 6,836,338 B2 | 12/2004 | Opsal et al. | |
| 6,844,965 B1 | 1/2005 | Engelhardt | |
| 6,847,452 B2 | 1/2005 | Hill | |
| 6,878,555 B2 | 4/2005 | Andersson et al. | |
| 6,891,791 B1 | 5/2005 | Gutin | |
| 6,897,965 B2 | 5/2005 | Ghadiri et al. | |
| 6,917,421 B1 | 7/2005 | Wihl et al. | |
| 6,917,432 B2 | 7/2005 | Hill et al. | |
| 6,918,404 B2 | 7/2005 | da Silva | |
| 6,937,323 B2 | 8/2005 | Worthington et al. | |
| 6,955,878 B2 | 10/2005 | Kambara et al. | |
| 6,958,131 B2 | 10/2005 | Tiefenthaler | |
| 6,980,299 B1 | 12/2005 | de Boer | |
| 6,980,677 B2 | 12/2005 | Niles et al. | |
| 6,987,569 B2 | 1/2006 | Hill | |
| 6,990,221 B2 | 1/2006 | Shams | |
| 6,992,769 B2 | 1/2006 | Gordon | |
| 6,995,845 B2 | 2/2006 | Worthington | |
| 7,006,927 B2 | 2/2006 | Yakhini et al. | |
| 7,008,794 B2 | 3/2006 | Goh et al. | |
| 7,012,249 B2 | 3/2006 | Krutchinsky et al. | |
| 7,014,815 B1 | 3/2006 | Worthington et al. | |
| 7,026,131 B2 | 4/2006 | Hurt et al. | |
| 7,027,163 B2 | 4/2006 | Angeley | |
| 7,031,508 B2 | 4/2006 | Lawless et al. | |
| 7,033,747 B2 | 4/2006 | Gordon | |
| 7,042,570 B2 | 5/2006 | Sailor | |
| 7,061,594 B2 | 6/2006 | Worthington et al. | |
| 7,066,586 B2 | 6/2006 | da Silva | |
| 7,070,987 B2 | 7/2006 | Cunningham et al. | |
| 7,077,996 B2 | 7/2006 | Randall et al. | |
| 7,083,920 B2 | 8/2006 | Werner et al. | |
| 7,087,203 B2 | 8/2006 | Gordon et al. | |
| 7,088,650 B1 | 8/2006 | Worthington et al. | |
| 7,091,034 B2 | 8/2006 | Virtanen | |

| | | |
|---|---|---|
| 7,091,049 B2 | 8/2006 | Boga et al. |
| 7,094,595 B2 | 8/2006 | Cunningham et al. |
| 7,094,609 B2 | 8/2006 | Demers |
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |
| 7,118,855 B2 | 10/2006 | Cohen et al. |
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | de Boer |
| 7,200,088 B2 | 4/2007 | Worthington et al. |
| 7,221,632 B2 | 5/2007 | Worthington et al. |
| 7,312,046 B2 | 12/2007 | Chin |
| 7,318,903 B2 | 1/2008 | Link |
| 7,345,770 B2 | 3/2008 | Chan et al. |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1 | 5/2002 | Demers |
| 2002/0065202 A1 | 7/2002 | Gordon |
| 2002/0097658 A1 | 7/2002 | Worthington et al. |
| 2002/0106661 A1 | 8/2002 | Virtanen et al. |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0078337 A1 | 4/2004 | King et al. |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1 | 8/2004 | Sorin |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0094956 A1* | 5/2005 | Parker et al. ............... 385/129 |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1 | 11/2005 | Tan et al. |
| 2005/0259260 A1 | 11/2005 | Wakita |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256350 A1 | 11/2006 | Nolte et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003925 A1 | 1/2007 | Nolte et al. |
| 2007/0003979 A1 | 1/2007 | Worthington |
| 2007/0023643 A1 | 2/2007 | Nolte et al. |
| 2007/0070848 A1 | 3/2007 | Worthington et al. |
| 2007/0077599 A1 | 4/2007 | Krutzik |
| 2007/0077605 A1 | 4/2007 | Hurt et al. |
| 2007/0108465 A1 | 5/2007 | Pacholski |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 2/1998 |
| WO | WO 0000265 | 1/2000 |
| WO | WO 0039584 | 7/2000 |
| WO | WO 0111310 | 2/2001 |
| WO | WO 0144441 | 6/2001 |
| WO | WO 2006042746 | 4/2006 |
| WO | WO 2006/075797 | 7/2006 |

OTHER PUBLICATIONS

S. Balasubramanian, L.Lahiri, Y. Ding, M.R. Melloch, and D.D. Nolte, Two-Wave Mixing Dynamics And Nonlinear Hot-Electron Transport In Transverse-Geometry Photorefractive Quantum Wells Studies By Moving Grantings, Appl. Phys. B. 68, pp. 863-869 (1990).

Bietsch, A. and B. Michel, Conformal Contact and Pattern Stability of Stamps Used For Soft Lithography, J. Appl. Phys., 2000, vol. 88, pp. 4310-4318.

Brecht, A. and Gauglitz, G., Recent Developments in Optical Transducers for Chemical or Biochemical Applications. Sensors and Actuators B, 1997 vol. 38-39, pp. 1-7.

E. Delmarche, A. Bernard, H. Schmid, B. Michel, and H. Biebuyck, Patterned Delivery of Immunoglobulins to Surface Using Microfluidic Networks, Science 276,779-781(1997).

E. Delamarche, A. Bernard, Schmid, B., Bietsch, Michel, and H. Biebuyck, Microfluidic Networks For Chemical Patterning of Substrates: Design and Application to Bioassays, Journal of the American Chemical Society 120, pp. 500-508 (1998).

A. Blouin et al., Detection of Ultrasonic Motion of a Scattering Surface by Two-Wave Mixing In a Photorefractive GaAs Crystal, Appl. Phys. Lett. 65, pp. 932-934 (1994).

P. Delaye, A. Blouin, D. Drolet, L.A. Montmorrillong, A. Roosen, and J.P. Monchalin, Detection of Ultrasonic Motion of a Scattering Surface by Photorefractive InP:Fe Under an Applied dc Field, J. Opt. Soc. Am. B14, pp. 1723-1734 (1997).

Ding, Y. et al., Femtosecond Pulse Shaping by Dynamic Holograms In Photorefractive Multiple Quantum Wells, Optical Society of America, Optics Letters, vol. 22, pp. 718-720, 1997.

Ding, Y. et al., Adaptive All-Order Dispersion Compensation of Ultrafast Laser Pulses Using Dynamic Spectral Holography, American Institute of Physics, Applied Physics Letters, vol. 77, pp. 3255-3257, 1999.

DuBendorfer, J. and Kunz, R. E., Reference Pads For Miniature Integrated Optical Sensors. Sensors and Actuators B, 1997, vol. 38-39, pp. 116-121.

Effenhauser, C.S., et al., Integrated Capillary Electrophoresis on Flexible Silicone Microdevices: Analysis of DNA Restriction Fragments and Detection of Single DNA Molecules on Microchips, Anal. Chem., 1997, vol. 69, pp. 3451-3457.

Ekins, R., F. Chu and E. Biggart, Development of Microspot Multi-Analyte Ratiometric Immunoassay Using Dual Flourescent-Labelled Antibodies. Anal. Chim. Acta, 1989, vol. 227, pp. 73-96.

Ekins R et al. Multianalyte Microspot Immunoassay, The Microanalytical Compact Disk of The Future: Clin. Chem., 1991, Vo. 37(11), p. 1955-1967.

Ekins, R., Ligand Assays, From Electrophoresis to Miniaturized Microarrays, Clin. Chem. 1998, vol. 44(9), pp. 2015-2030.

Fattinger, C., Koller, H., Schlatter, D., Wehrli, P., 1993, The Difference Interferometer-A High Sensitive Optical Probe For Quantification of Molecular-Surface Concentration, Biosens, Bioelectron 8, pp. 99-107.

Gao, H., et al., Immunosensing With Photo-Immobilized Immunoreagents on Planar Optical Wave Guides. Biosensors and Bioelectronics, 1995, vol. 10, pp. 317-328.

Geissler. M. et al., Microcontact Printing Chemical Patterns With Flat Stamps, J. Am. Chem. Soc., 2000, vol. 122, pp. 6303-6304.

Gruska, B. et al., Fast and Reliable Thickness and Refractive Index Measurement of Antireflection Coatings on Solar-Silicon by Ellipsometry, Sentech Instruments GmbH, CarlOScheele-Str. 16, 12489 Berlin Germany, Sep. 2006.

Grzybowski, B.A., et al., Generation of Micrometer-Sized Patterns For Microanalytical Applications Using a Lasar Direct-Write Method and Microcontact Printing, Anal. Chem., 1998, vol. 70, pp. 4645-4652.

Hagman, M., Doing Immunology on a Chip, Science. 2000, vol. 290, pp. 82-83.

He, B. and F.E. Regnier, Fabrication of Nanocolumns for Liquid Chromatography, Anal. Chem., 1998, vol. 70, pp. 3790-3797.

Hecht, E., Optics, 1987, Addison-Wesely Publishing Co., Inc., Menlo Park, CA, pp. 281-286.

Hu, J. et al., Using Soft Lithography to Fabricate GaAs/AlGaAs Heterostructure Field Effect Transistors. Appl. Phys. Lett., 1997 vol. 71, pp. 2020-2022.

Ing R.K. and Monchalin, L.P., Broadband Optical Detection of Ultrasound by Two-Wave Mixing In a Photorefractive Crystal, Appl. Phys. Lett. 59, 3233-5 (1991).

Jenison, R., Yan, S. Haeberli, A. Polisky, B., 2001, Interference-Based Detection of Nucleic Acid Targets on Optically Coated Silicon. Nat. Biotechnol. 19, pp. 62-65.

Jenison, Robert et al. Silicon-based Biosensors for Rapid Detection of Protein or Nucleic Acid Targets, Clinical Chemistry, 47:10, 2001 pp. 1894-1990.

Jones, R. et al., Adaptive Femtosecond Optical Pulse Combining, American Institiute of Physics, pp. 3692-3694, 2000.

Kapur, Ravi et al. Streamlining the Drug Discovery Process by Integrating Miniaturization High Throughput Screening, High Content Screening, and Automation on the CeliChip TM System. Biomedical Microdevices, vol. 3, No. 2, 1999, pp. 99-109.

Kricka, L.J., Miniaturization of Analytical Systems. Clin. Chem., 1998, vol. 44(9), pp. 2008-2014.

Kunz, R. E., Miniature Integrated Optical Modules For Chemical and Biochemical Sensing. Sensors and Actuators B, 1997, vol. 38-39, pp. 13-28.

Kwolek, K.M. et al., Photorefractive Asymmetric Fabry-Perot Quantum Wells: Transverse-field Geometry, Appl. Phys. Lett, vol. 67, pp. 736-738, 1995.

La Clair, J. et al., Molecular Screening on a Compact Disc, The Royal Society of Chemistry, Org. Biomol. Chem., vol. 1, pp. 3244-3249, 2003.

Lahiri, I. et al., Photorefractive p-i-n Diode Quantum Well Spatial Light Modulators, American Institute of Physics, Applied Physics Letters, vol. 67, pp. 1408-1410, 1995.

I. Lahiri, L.J. Pyrak, Nolte, D.D. Nolte, M.R Melloch, RA. Kruger, G.O. Backer, and M. B. Klein, Laser-Based Ultrasound Detection Using Photorefractive Uantum Wells, Appl. Phys. Lett. 73, pp. 1041-1043 (1998).

Maisenholder, B., et al. A GaAs/A1GaAs-based Refractometer Platform For Integrated Optical Sensing Applications, Sensors and Actuators S, 1997, vol. 38-39, pp. 324-329.

Martin, B.D., et al., Direct Protein Microarray Fabrication Using a Hydrogel Stamper, Langmuir, 1998, vol. 14, pp. 3971-3975.

Marx, J., DNA Arrays Reveal Cancer In Its Many Forms, Science, 2000, vol. 289, pp. 1670-1672.

Montmorillon, La Biaggi0, I Delaye, P, Launay, J.C., and Roosen, A, Eye Safe Large Field of View Homodyne Detection Using a Photorefractive CdTe:V Crystal. Opt. Commun. 29, pp. 293 (1996).

Morhard, F. et al., Immobilization of Antibodies In Micropatterns For Cell Detection by Optical Diffraction, Sensors and Actuators B, 2000, vol. 70, pp. 232-242.

Nolte, D.D., Semi-Insulating Semiconductor Heterostructures: Optoelectronic Properties and Applications, Appl. Phys. vol. 85, pp. 6259-6289, 1999.

Nolte, D. D. et al., Adaptive Beam Combining and Interferometry Using Photorefractive Quantum Wells, J. Opt. Soc. Am. B, vol. 19, No. 2, Feb. 2001, pp. 195-205.

Nolte, D.D. et al., Spinning-Disk Interferometry The BioCD, Optics & Photonics News, pp. 48-53, 2004.

Nolte, D. D., Self-Adaptive Optical Holography In Quantum Wells, pp. 1-6, 2005.

Nolte, D., et al., Photorefractive Quantum Wells, 2005.

Peng, Leilei et al., Adaptive Optical Biocompact Disk For Molecular Recognition, Applied Physics Letters 86, pp. 183902-1-183902-3, 2005.

Pompe, T., et al., Submicron Contact Printing on Silicon Using Stamp Pads, Langmuir, 1999, vol. 15, pp. 2398-2401.

Pouet. S.F., Ing. R.K., Krishnaswanry S. and Royer D. Heterodyne Interferometer With Two-Wave Mixing In Photo refractive Crystals For Ultrasound Detection on Rough Surface, Appl. Phys. Lett. 69. pp. 3782 (1996).

Regnier, F.E., et al. Chromatography and Electrophoresis on Chips: Critical Elements of Future Integrated, Microfluidic Analytical Systems For Life Science. Tibtech, 1999, vol. 17, pp. 101-106.

I. Rossomakhin and Stepanov, Linear Adaptive Interferometers Via Diffusion Recording In Cubic Photorefractive Crystals, Opt. Commun. 86, pp. 199-204 (1991).

Sanders, G.H.W. and A. Manz, Chip-based Microsystems For Genomic and Proteomic Analysis, Trends in Anal, Chem., 2000, vol. 19(6), pp. 364-378.

Scruby, C.B. and L.E. Drain, Lasar Ultrasonics: Techniques and Applications. 1990, Bristol: Adam Hilger., pp. 116-123.

Varma, M.M, et al., Spinning-Disk Self-Referencing Interferometry of Antigen-Antibody Recognition, Optics Letters, vol. 29. pp. 950-952, 2004.

Wang, J., Survey and Summary From DNA Biosensors To Gene Chips. Nucl. Acids Res., 2000 vol. 28 (16), pp. 3011-3016.

See, C.W. et al., Scanning Differential Optical Profilometer For Simultaneous Measurement of Amplitude and Phase Variation, Appl. Phys. Lett, vol. 53, No. 1, pp. 10-12, 1988.

Somekh, Michael et al., Scanning Heterodyne Confocal Differential Phase and Intensity Microscope, Applied Optics, vol. 34, No. 22, pp. 4857-4868, 1995.

Burkhart, et al. UCSD Scientists Develop Novel Way to Screen Molecules Using Conventional CDS an Compact Disk Players; UCSD newsletter; pp. 1-4, 2003.

Xia, Y., et al. Non Photolithographic Methods and Fabrication of Elastomeric Stamps for Use in Microcontact Printing, Langmuir, 1996, Vo. 12, pp. 4033-4038.

Suddendorf. Manfred, et al., Single-Probe-Beam Differential Amplitude and Phase-Scanning Interferometer, Applied Optics, vol. 36, No. 25, pp. 6202-6210, 1997.

Varma, M.M. et al.: High-Speed Label-Free Multi-Analyte Detection Through Micro-Interferometry, Proc. of SPIE, vol. 4966, pp. 58-64. 2003.

Varma, M.M., et al., High Speed Label Free Detection By Spinning-Disk Micro-Interferometry, Biosensors & Bioelectronics, vol. 19, pp. 1371-1376, 2004.

St. John et al., Diffraction-Based Cell Detection Using a Microcontact Printed Antibody Grating, Analytical Chemistry, 1998, vol. 70, No. 6, pp. 1108-1111.

Musundi et al., "Approaching Real-Time Molecular Diagnostics: Single-Pair Fluorescence Resonance Energy Transfer (spFRET) Detection for the Analysis of Low Abundant Point Mutations in K-ras Oncogenes," J Am Chem Soc. Jun. 11, 2003;125(23):6937-45.

Lovgren J, Valtonen-Andre C, Marsal K, et al.: Measurement of prostate-specific antigen and human glandular kallikrein 2 in different body fluids. J. Androl. 20:348-355, 1999.

J. Homola, "Present and future of surface plasmon resonance biosensors," Analytical and Bioanalytical Chemistry, vol. 377, pp. 528-539, 2003.

Nolte, David D. (2007), "Molecular Interferometry", http://www.nanohub.org/resources/2832/, Jun. 26, 2007 (67 pages).

Michele Ceccarelli, Giuliano Antoniol: A Deformable Grid-Matching Approach for Microarray Images. IEEE Transactions on Image Processing 15(10): 3178-3188 (2006).

Peter Bajcsy: Gridline: automatic grid alignment DNA microarray scans. IEEE Transactions on Image Processing 13(1): 15-25 (2004).

Luis Rueda, Vidya Vidyadharan: A Hill-Climbing Approach for Automatic Gridding of cDNA Microarray Images. IEEE/ACM Trans. Comput. Biology Bioform. 3(1): 72-83 (2006).

Nagarajan, R., Intensity-based segmentation of microarrays images. IEEE Trans. Med. Imaging. v22. 882-889 (2003).

Faramarzpour, N., Shirani, S. and Bondy, J., Lossless DNA microarray image compression. IEEE Conf. Signal Systems Comput. v2. 1501-1504 (2003).

Katzer, M., Kummert, F. and Sagerer, G., Methods for automatic microarray image segmentation. IEEE Trans. NanoBiosci. v2 i4. 202-214 (2003).

N. Brändle, H. Bischof, H. Lapp: *"Robust DNA Microarray Image Analysis"*; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Konstantinos Blekas, Nikolas P. Galatsanos, Aristidis Likas, Isaac E. Lagaris: Mixture model analysis of DNA microarray images. IEEE Trans. Med. Imaging 24(7): 901-909 (2005).

Jinn Ho, Wen-Liang Hwang, Henry Horn-Shing Lu, and D. T. Lee, 'Gridding Spot Centers of Smoothly Distorted Microarray Images', IEEE Trans. on Image Processing, vol. 15, No. 2, Feb. 2006.

Fabri, R: "Towards non-parametric gridding of Microarray images," Digital Signal Processing. 2002. DSP 2002. 2002 14th International Conference publication, vol. 2, pp. 623-626.

H. Vikalo, B. Hassibi, and A. Hassibi, "A statistical model for microarrays, optimal estimation algorithms, and limits of performance," IEEE Transactions on Signal Processing, Special Issue on Genomics Signal Processing, vol. 54, No. 6, Jun. 2006, pp. 2444-2455.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

MacBeath, G. and S.L. Schreiber. 2000. "Printing proteins as microarrays for high-throughput function determination." Science 289:1760-1763.

Guemouri, L., J. Ogier, and J. J. Ramsden, "Optical properties of protein monolayers during assembly." Journal of Chemical Physics 1998. 109:3265-3268.

Ostroff, R., A. Ettinger, H. La, M. Rihanek, L. Zalman, J. Meador III, A. K. Patick, S. Worland, and B. Polisky. 2001. "Rapid multiserotype detection of human rhinoviruses on optically coated silicon surfaces." J. Clin. Virol. 21: 105-117.

H. Ozen and S. Sozen, "PSA Isoforms in prostate cancer detection," *Eur. Urol. Suppl.*, vol. 5, pp. 495-499, 2006.

N. B. Sheller, S. Petrash, M.D. Foster, "Atomic Force Microscopy and X-ray Reflectivity Studies of Albumin Adsorbed onto Self-Assembled Monolayers of Hexadecyltrichlorosilane," *Langmuir*, 14, 4535-4544, 1998.

M. Varma, D. D. Nolte, H. D. Inerowicz, and F. E. Regnier, "Multi-Analyte Array Micro-Diffraction Interferometry," in *Microarrays: Design, Fabrication and Reading*, vol. 4626, B. J. B. e. al., Ed.: SPIE, 2002, pp. 69-77.

D. D. Nolte and M. R. Melloch, "Photorefractive Quantum Wells and Thin Films," in *Photorefractive Effects and Materials*, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric Fabry-Perot Reflection Modulator with very High Contrast Ratio," *IEEE Phot. Tech. Lett.*, vol. 5, pp. 55-58, 1993.

M. Whitehead and G. Parry, "High-contrast reflection modulation at normal incidence in asymmetric multiple quantum well Fabry-Perot structure," *Electron. Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated optical Mach-Zehnder interferometers as simazine immunoprobes," *Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Heller, "Microelectronic array devices and techniques for electric field enhanced DNA hybridization in low-conductance buffers," *Electrophoresis*, vol. 23, pp. 1543-1550, 2002.

Y. Joon Mo, J. Bell, H. Ying, M. Tirado, D. Thomas, A. H. Forster, R. W. Haigis, P. D. Swanson, R. B. Wallace, B. Martinsons, and M. Krihak, "An integrated, stacked microlaboratory for biological agent detection with DNA and immunoassays," *Biosensors & Bioelectronics*, vol. 17, pp. 605-618, 2002.

M. J. Heller, "An active microelectronics device for multiplex DNA analysis," *IEEE Engineering in Medicine & Biology Magazine*, vol. 15, pp. 100-104, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal Fabry-Perot electrooptic modulators," *IEEE Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," *Appl. Phys. Lett.*, vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

S. P. Balk, Y.-J. Ko, and G. J. Bubley, "Biology of Prostate-specific antigen," J. Clin. Onc., vol. 21, pp. 383-391, 2003.

Wang, M.C., Papsidero, L.D., Kuriyama, M., Valenzuela, G.P. and Chu, T.M. 1981. Prostate antigen: A new potential marker for prostatic cancer. *The Prostate* 2: 89-96.

T. Cass and F. S. Ligler, "Immobilized Biomolecules in Analysis: A Practical Approach," Oxford: Oxford, 1998.

R. Guersen, I. Lahiri, M. R. Melloch, J. M. Woodall and D. D. Nolte, Transient Enhanced Intermixing of Arsenic-Rich Nonstoichiometric AlAs/GaAs Quantum Wells, Phys. Rev. B60,10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. McKenna, D. D. Nolte, W. Walukiewicz, and P. Becla, "Persistent holographic absorption gratings in AlSb:Se," *Appl. Phys. Lett.*, vol. 68, pp. 735-737, 1996.

R. S. Rana, E. Oh, K. Chua, A. K. Ramdas, and D. D. Nolte, "Voigt photorefractive two-wave mixing in CdMnTe," *J. Lumin.*, vol. 60&61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effective-mass AlGaAs/GaAs Fibonacci superlattices," *Phys. Rev. B*, vol. 56, pp. 1987-1995, 1997.

M. Dinu, K. Nakagawa, M. R. Melloch, A. M. Weiner, and D. D. Nolte, "Broadband Low-Dispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwidth Study of Volume Holography in Photorefrative InP:Fe at 1.5 microns for Frequency Domain Femtosecond Pulse Processing," *J. Opt. Soc. B*, vol. 15, pp. 2763-2768, 1998.

Y. Ding, I. Lahiri, D. D. Nolte, G. J. Dunning, and D. M. Pepper, "Electric Field Correlation of Femtosecond Pulses Using a Photo-Electromotive Force Detector," *J. Opt. Soc. Am. B*, vol. 15, pp. 2013-2017, 1998.

R. Jones, N. P. Barry, S. C. W. Hyde, P. M. W. French, K. M. Kwolek, D. D. Nolte, and M. R. Melloch, "Direct-to-Video holographic readout in quantum wells for 3-D imaging through turbid media," *Opt. Lett.*, vol. 23, pp. 103-105, 1998.

R. Jones, M. Tziraki, P. M. W. French, K. M. Kwolek, D. D. Nolte, and M. R. Melloch, "Direct-to-video holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B*, vol. 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-365, 1999.

I. Lahiri, D. D. Nolte, M. R. Melloch, and M. B. Klein, "Oscillatory mode coupling and electrically strobed gratings in photorefractive quantum-well diodes," *Optics Lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2, pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

D. M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct. Eval.*, vol. 17, pp. 627-634, 1998.

D. D. Nolte, *Mesoscopic Pointlike Defects in Semiconductors: Deep-level Energies*, Phys. Rev. B 58, 7994-8001 (1998).

M. Dinu, I. Miotkowski and D. D. Nolte, *Magnetic Quenching of Time-Reversed Light in Photorefractive Diluted Magnetic Semiconductors*, Phys. Rev. B 58, 10435 (1998).

S. Balasubramanian, S. W. Mansour, M. R. Melloch and D. D. Nolte, *Vacancy diffusion Kinetics in arsenic-rich nonstoichiometric AlAs/GaAs heterostructures*, Phys. Rev. B 63, 033305-1-033305-3 (2000).

David D. Nolte, Manoj M. Varma, Leilei Peng, Halina D. Inerowicz, Fred E. Regnier, *Spinning-disk laser interferometers for immunoassays and proteomics: the BioCD* in Proc. SPIE vol. 5328,, Microarrays and Combinatorial Techniques: Design, Fabrication, and Analysis II; Dan V. Nicolau, Ramesh Raghavachari; Eds., p. 41-48 (2004).

Manoj M. Varma, Halina D. Inerowicz, Fred E. Regnier, David D. Nolte, *Real-time spinning-disk interferometric immunoassays*, in Proc. SPIE vol. 5328, Microarrays and Combinatorial Techniques: Design, Fabrication, and Analysis II; Dan V. Nicolau, Ramesh Raghavachari; Eds., p. 62-68 (2004).

T. Jensen, L. Kelly, A. Lazarides, and G. C. Schatz, "Electrodynamics of noble metal nanoparticles and nanoparticle clusters," *Journal of Cluster Science*, vol. 10, pp. 295-317, 1999.

H. Kuwata, H. Tamaru, K. Esumi, and K. Miyano, "Resonant light scattering from metal nanoparticles: Practical analysis beyond Rayleigh approximation," *Applied Physics Letters*, vol. 83, pp. 4625-4627, 2003.

M.J. Jory, P. S. Cann, J. R. Sambles, and E. A. Perkins, "Surface-plasmon-enhanced light scattering from microscopic spheres," *Applied Physics Letters*, vol. 83, pp. 3006-3008, 2003.

K.L. Kelly, E. Coronado, L. L. Zhao, and G. C. Schatz, "The optical properties of metal nanoparticles: The influence of size, shape, and dielectric environment," *Journal of Physical Chemistry B*, vol. 107, pp. 668-677, 2003.

P. Chakraborty, "Metal nanoclusters in glasses as non-linear photonic materials," *Journal of Materials Science*, vol. 33, pp. 2235-2249, 1998.

S.J. Oldenburg, S. L. Westcott, R. D. Averitt, and N. J. Halas, "Surface enhanced Raman scattering in the near infrared using metal nanoshell substrates," *Journal of Chemical Physics*, vol. 111, pp. 4729-4735, 1999.

P. Mulvaney, "Surface plasmon spectroscopy of nanosized metal particles," *Langmuir*, vol. 12, pp. 788-800, 1996.

H.F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779-6782, 1998.

T.W. Ebbesen, H. J. Lezec, H. F. Ghaemi, T. Thio, and P. A. Wolff, "Extraordinary optical transmission through sub-wavelength hole arrays," *Nature*, vol. 391, pp. 667-669, 1998.

D.A. Genov, A. K. Sarychev, V. M. Shalaev, and A. Wei, "Resonant field enhancements from metal nanoparticle arrays," *Nano Letters*, vol. 4, pp. 153-158, 2004.

V. Koubova, E. Brynda, L. Karasova, J. Skvor, J. Homola, J. Dostalek, P. Tobiska, and J. Rosicky, "Detection of foodborne pathogens using surface plasmon resonance biosensors," Sensors and Actuators B-Chemical, vol. 74, pp. 100-105, 2001.

M. Minunni, and M. Mascini, "Detection of Pesticide in Drinking-Water Using Real-Time Biospecific Interaction Analysis (Bia)," *Analytical Letters*, vol. 26, pp. 1441-1460, 1993.

C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," Analytica Chimica Acta, vol. 338, pp. 109-117, 1997.

A. Rasooly, "Surface plasmon resonance analysis of staphylococcal enterotoxin B in food," *Journal of Food Protection*, vol. 64, pp. 37-43, 2001.

G. Sakai, K. Ogata, T. Uda, N. Miura, and N. Yamazoe, "A surface plasmon resonance-based immunosensor for highly sensitive detection of morphine," Sensors and Actuators B-Chemical, vol. 49, pp. 5-12, 1998.

G. Sakai, S. Nakata, T. Uda, N. Miura, and N. Yamazoe, "Highly selective and sensitive SPR immunosensor for detection of methamphetamine," Electrochimica Acta, vol. 44, pp. 3849-3854, 1999.

E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.

A. Otto, "Excitation of Nonradiative Surface Plasma Waves in Silver by Method of Frustrated Total Reflection," *Zeitschrift Fur Physik*, vol. 216, pp. 398-410, 1968.

J. Homola, S. S. Yee, and G. Gauglitz, "Surface plasmon resonance sensors: review," Sensors and Actuators B-Chemical, vol. 54, pp. 3-15, 1999.

M. Malmqvist, "Biacore: an affinity biosensor system for characterization of biomolecular interactions," *Biochemical Society Transactions*, vol. 27, 1999.

M. Fivash, E. M. Towler, and R. J. Fisher, "BIAcore for macromolecular interaction," Current Opinion in Biotechnology, vol. 9, pp. 97-101, 1998.

L.D. Roden and D. G. Myszka, "Global analysis of a macromolecular interaction measured on BIAcore," Biochemical and Biophysical Research Communications, vol. 225, pp. 1073-1077, 1996.

C.F. R. Mateus, M. C. Y. Huang, B. T. Cunningham, and C. J. Chang-Hasnain, "Compact label-free biosensor using VCSEL-based measurement system," Ieee Photonics Technology Letters, vol. 16, pp. 1712-1714, 2004.

P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.

G. Walter, K. Bussow, A. Lueking, and J. Glokler, "High-throughput protein arrays: prospects for molecular diagnostics," Trends in Molecular Medicine, vol. 8, pp. 250-253, 2002.

J.B. Pendry, L. Martin-Moreno, and F. J. Garcia-Vidal, "Mimicking surface plasmons with structured surfaces," Science, vol. 305, pp. 847-848, 2004.

A.G. Brolo, R. Gordon, B. Leathem, and K. L. Kavanagh, "Surface plasmon sensor based on the enhanced light transmission through arrays of nanoholes in gold films," Langmuir, vol. 20, pp. 4813-4815, 2004.

J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.

J. Coy, F. Stedt, I. Lahiri, M. Melloch, and D. Nolte, "Exciton electroabsorption moments and sum rules," Opt. Commun., vol. 176, pp. 17-29, 2000.

R. S. Rana, E. Oh, K. Chua, A. K. Ramadas, and D. D. Nolte, "Magneto-photorefractive effects in a diluted magnetic semiconductor," *Phys. Rev. B*, vol. 49, pp. 7941-7951, 1994.

D. D. Nolte, I. Lahiri, J. McKenna, F. R. Steldt, J. C. P. Chang, M. R. Melloch, and J. M. Woodall, "Wannier excitons in a Coulomb Cage," presented at 23rd Int. Conf. Phys. Semicond., Vancouver, Canada, 1994.

D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.

D. M. Pepper, G. J. Dunning, D. D. Nolte, J. Coy, M. B. Klein, G. D. Bacher, and B. Pouet, "Enhanced Responsivity of Photo-Induced-emf Laser Ultrasound Sensors Using Asymmetric Interdigitated Contacts," in Review of Progress in Quantitative Nondestructive Evaluation, vol. 19, D. O. Thompson and D. E. Chimenti, Eds. New York: American Institute of Physics Press, 2000, pp. 2013-2020.

Technology paper entitled "Grating-Coupled Surface Plasmon Resonance (GCSPR)"—printed from HTS Biosystems Technologies website (www.htsbiosystems.com/technology/gcspr.htm) on May 2, 2005.

B. Cunningham, P. Li, and J. Pepper, "Colorimetric resonant reflection as a direct biochemical assay technique," Sensors and Actuators B, vol. 81, pp. 316-328, 2002.

X. Wang, M. Zhao, and D. D. Nolte, "Common-path interferometric detection of protein monolayer on the BioCD," Appl. Opt. 46, 7836-7849 (2007).

X. Wang and D. Nolte, "The Bragg Side-Band BioCD," in Conference on Lasers and Electro-Optics/Quantum Electronics and Laser Science Conference and Photonic Applications Systems Technologies, OSA Technical Digest (CD) (Optical Society of America, 2007), 2 pages.

Polizzi, M.A., Plocinik, R.M., and Simpson, G.J., "Ellipsometric Approach for the Real-Time Detection of Label-Free Protein Adsorption by Second Harmonic Generation," J. Am. Chem. Soc., 126, 15, 5001-5007, 2004.

Plocinik, R. M.; Simpson, G. J., Polarization characterization in surface second harmonic generation by nonlinear optical null ellipsometry. Analytica Chimica Acta 2003, 496, (1-2), 133-142.

P. B. Luppa, L. J. Sokoll, and D. W. Chan, "Immunosensors—principles and applications to clinical chemistry," *Clinica Chimica Acta*, vol. 314, pp. 1-26, 2001.

C. L. Tucker, J. F. Gera, and P. Uetz, "Towards an understanding of complex protein networks," *Trends In Cell Biology*, vol. 11, pp. 102-106, 2001.

P. Uetz and R. L. Finley, "From protein networks to biological systems," *Febs Letters*, vol. 579, pp. 1821-1827, 2005.

G. Gauglitz, "Direct optical sensors: principles and selected applications," Analytical and Bioanalytical Chemistry, vol. 381, pp. 141-155, 2005.

M. Zhao, D. D. Nolte, W. R. Cho, F. Regnier, M. Varma, G. Lawrence, and J. Pasqua, "High-speed interferometric detection of label-free immunoassays on the biological compact disc," *J. Clin. Chem.*, vol. 52, pp. 2135-2140, 2006.

David D. Nolte and Ming Zhao, "*Scaling mass sensitivity of the BioCD at 0.25 pg/mm*," Proc. SPIE Int. Soc. Opt. Eng. 6380, 63800J (2006), DOI: 10.1117/12.686307 (6 pages).

* cited by examiner

METHOD AND APPARATUS FOR CONJUGATE QUADRATURE INTERFEROMETRIC DETECTION OF AN IMMUNOASSAY

CROSS-REFERENCE TO RELATED APPLICATIONS

This application claims the benefit of U.S. Provisional Patent Application Ser. No. 60/896,979, filed Mar. 26, 2007, the disclosure of which is incorporated in its entirety herein by this reference. This application is also related to U.S. application Ser. No. 11/675,359, filed on Feb. 15, 2007, entitled "In-Line Quadrature and Anti-Reflection Enhanced Phase Quadrature Interferometric Detection"; U.S. patent application Ser. No. 10/726,772, entitled "Adaptive Interferometric Multi-Analyte High-Speed Biosensor," filed Dec. 3, 2003 (published on Aug. 26, 2004 as U.S. Pat. Publication No. 2004/0166593), which is a continuation-in-part of U.S. Pat. No. 6,685,885, filed Dec. 17, 2001 and issued Feb. 3, 2004, the disclosures of which are all incorporated herein by this reference. This application is further related to U.S. patent application Ser. No. 11/345,462 entitled "Method and Apparatus for Phase Contrast Quadrature Interferometric Detection of an Immunoassay," filed Feb. 1, 2006; and also U.S. patent application Ser. No. 11/345,477 entitled "Multiplexed Biological Analyzer Planar Array Apparatus and Methods," filed Feb. 1, 2006; and also U.S. patent application Ser. No. 11/345,564, entitled "Laser Scanning Interferometric Surface Metrology," filed Feb. 1, 2006; and also U.S. patent application Ser. No. 11/345,566, entitled "Differentially Encoded Biological Analyzer Planar Array Apparatus and Methods," filed Feb. 1, 2006, the disclosures of which are all incorporated herein by this reference.

BACKGROUND OF THE INVENTION

In many chemical, biological, medical, and diagnostic applications, it is desirable to detect the presence of specific molecular structures in a sample. Many molecular structures such as cells, viruses, bacteria, toxins, peptides, DNA fragments, and antibodies are recognized by particular receptors. Biochemical technologies including gene chips, immunological chips, and DNA arrays for detecting gene expression patterns in cancer cells, exploit the interaction between these molecular structures and the receptors. [For examples, see the descriptions in the following articles: Sanders, G. H. W. and A. Manz, *Chip-based microsystems for genomic and proteomic analysis*. Trends in Anal. Chem., 2000, Vol. 19(6), p. 364-378. Wang, J., *From DNA biosensors to gene chips*. Nucl. Acids Res., 2000, Vol. 28(16), p. 3011-3016; Hagman, M., *Doing immunology on a chip*. Science, 2000, Vol. 290, p. 82-83; Marx, J., *DNA Arrays reveal cancer in its many forms*. Science, 2000, Vol. 289, p. 1670-1672]. These technologies generally employ a stationary chip prepared to include the desired receptors (those that interact with the target analyte or molecular structure under test). Since the receptor areas can be quite small, chips may be produced which test for a plurality of analytes. Ideally, many thousand binding receptors are used to provide a complete assay. When the receptors are exposed to a biological sample, only a few may bind a specific protein or pathogen. Ideally, these receptor sites are identified in as short a time as possible.

One such technology for screening for a plurality of molecular structures is the so-called immunological compact disk, which simply includes an antibody microarray. [For examples, see the descriptions in the following articles: Ekins, R., F. Chu, and E. Biggart, *Development of microspot multi-analyte ratiometric immunoassay using dual flourescent-labelled antibodies*. Anal. Chim. Acta, 1989, Vol. 227, p. 73-96; Ekins, R. and F. W. Chu, *Multianalyte microspot immunoassay—Microanalytical "compact Disk" of the future*. Clin. Chem., 1991, Vol. 37(11), p. 1955-1967; Ekins, R., *Ligand assays: from electrophoresis to miniaturized microarrays*. Clin. Chem., 1998, Vol. 44(9), p. 2015-2030]. Conventional fluorescence detection is employed to sense the presence in the microarray of the molecular structures under test. Other approaches to immunological assays employ traditional Mach-Zender interferometers that include waveguides and grating couplers. [For examples, see the descriptions in the following articles: Gao, H., et al., *Immunosensing with photo-immobilized immunoreagents on planar optical wave guides*. Biosensors and Bioelectronics, 1995, Vol. 10, p. 317-328; Maisenholder, B., et al., *A GaAs/AlGaAs-based refractometer platform for integrated optical sensing applications*. Sensors and Actuators B, 1997, Vol. 38-39, p. 324-329; Kunz, R. E., *Miniature integrated optical modules for chemical and biochemical sensing*. Sensors and Actuators B, 1997, Vol. 38-39, p. 13-28; Dübendorfer, J. and R. E. Kunz, *Reference pads for miniature integrated optical sensors*. Sensors and Actuators B, 1997 Vol. 38-39, p. 116-121; Brecht, A. and G. Gauglitz, *recent developments in optical transducers for chemical or biochemical applications*. Sensors and Actuators B, 1997, Vol. 38-39, p. 1-7]. Interferometric optical biosensors have the intrinsic advantage of interferometric sensitivity, but are often characterized by large surface areas per element, long interaction lengths, or complicated resonance structures. They also can be susceptible to phase drift from thermal and mechanical effects.

While the abovementioned techniques have proven useful for producing and reading assay information within the chemical, biological, medical and diagnostic application industries, developing improved fabrication, reading and performance techniques is desirable. As such, the present invention is intended to address one or more of the problems discussed above.

SUMMARY OF THE INVENTION

According to one aspect of the present invention, a detection system for detecting target material is provided. According to this aspect of the invention, the system comprises a photonic structure having a reflectance-band and associated side bands; an illumination source for illuminating at a wavelength in at least one of an edge of the reflectance-band and the side bands of the photonic structure and for generating a return beam; a detector system having an intensity-sensitive channel configured to detect an in-line signal from the return beam and a phase-sensitive channel configured to detect a differential phase contrast signal from the return beam; and a processing system for receiving and adding in quadrature the in-line signal and the differential phase contrast signal to generate a joint signal, and for determining one of the presence or the absence of the target material on the photonic structure using the joint signal.

In another aspect of the present invention, a method for detecting the presence of an antigen on a photonic structure is provided. According to this aspect of the invention, the method comprises exposing the photonic structure to a sample that may contain the antigen, the photonic structure having a reflectance-band and side bands; illuminating at a wavelength at least one of an edge of the reflectance-band and the side bands of the photonic structure with an illumination source to create a return beam; detecting the return beam with a detector system having an intensity-sensitive detection function and a phase-sensitive detection function; detecting an in-line quadrature signal from the return beam using the intensity-sensitive detection function of the detector system; detecting a differential phase contrast quadrature signal from the return beam using the phase-sensitive detection function of the detector system; receiving the in-line quadrature signal and the differential phase contrast quadrature signal; combining the in-line quadrature signal and the differential phase contrast quadrature signal to generate a joint signal, and determining one of the presence or the absence of the target material on the photonic structure using the joint signal.

In yet another aspect of the present invention, a method for using a resonant response modulus to provide a signal robust against operating system drift is provided. According to this aspect of the invention, the method comprises providing a substrate including a plurality of target molecules distributed about the substrate; illuminating the substrate with a illumination source to produce a reflected beam and cause a resonant response; detecting the modulus of the resonant response with a photodetector by separately detecting an in-phase intensity resonant response and a conjugate phase resonant response; and combining the in-phase intensity resonant response and the conjugate phase resonant response to provide a signal robust against operating system drift, the signal being representative of the detected modulus of the combined responses.

BRIEF DESCRIPTION OF THE DRAWINGS

This application contains at least one drawing executed in color. Copies of this patent or patent application publication with color drawing(s) will be provided by the Patent Office upon request and payment of the necessary fee.

The above-mentioned aspects of the present invention and the manner of obtaining them will become more apparent and the invention itself will be better understood by reference to the following description of the embodiments of the invention taken in conjunction with the accompanying drawings, wherein.

DETAILED DESCRIPTION

Figure 1:
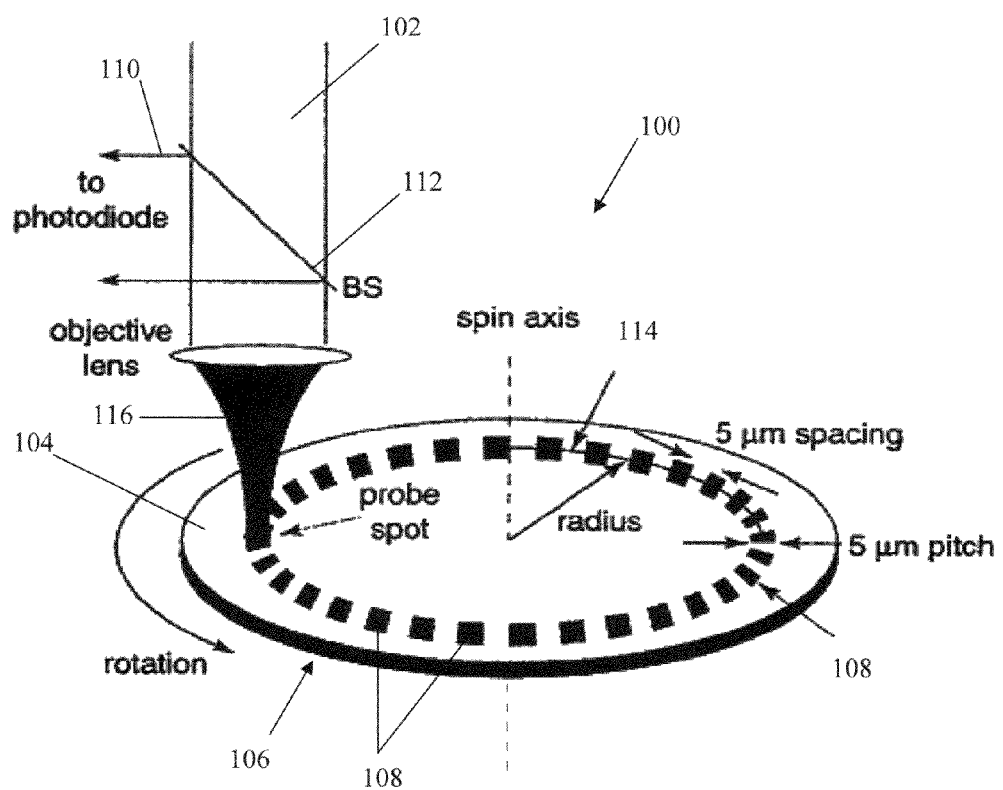
FIG. 1 depicts an exemplary spinning-disk self-referencing interferometric laser scanning detection system in accordance with the present invention.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In quadrature interference, the presence of protein causes a small phase shift in a signal beam that interferes with a reference beam, which is about $\pi/2$ or $3\pi/2$ out of phase. Embodiments using common-path interferometry locally produce signal and reference beams so that they share common optical paths. Moreover, the relative phase difference is locked at about $\pi/2$ and is unaffected by mechanical vibration or motion. By working at quadrature, the total interference intensity shift changes linearly and with maximum slope as a function of the phase shift caused by proteins. Moreover, by working with a high-speed spinning disk, the typical 1/f system noise has a 40 dB per octave slope. Furthermore, at a frequency well above the 1/f noise, a 50 dB noise floor suppression can be obtained, thereby making it possible to measure protein signals with high precision.

Several different quadrature classes have been reported, each of which differ in the way they establish their quadrature condition. One such class is the micro-diffraction class ("MD-class"), which uses gold microstructures that are $\lambda/8$ in height to set the phase difference between the light reflected from the gold structure and the substrate. Quadrature is locked using microstructures fabricated on the disk that diffract a focused laser beam to the far field with a fixed relative phase. In one embodiment, gold spokes having a height of $\lambda/8$ are deposited by evaporation onto a reflecting surface, and bio-molecules are immobilized on either the gold spokes or the land. Because the phase difference is set by the height difference of the local microstructure, it is unaffected by mechanical motion or vibration. Immobilized bio-molecules change the relative phase, which is converted to amplitude modulation in the far field. For further details of the MD-class, see U.S. patent application Ser. No. 10/726,772 filed Dec. 3, 2003, entitled "Adaptive Interferometric Multi-Analyte High-Speed Biosensor," which was previously incorporated by reference in its entirety.

Another exemplary quadrature class in accordance with the present teachings is the adaptive-optic quadrature class ("AO-class"), which was introduced using self-adaptive nonlinear optical mixing in a photorefractive quantum well to adaptively track the phase difference between signal and reference beams. In one embodiment, patterned protein structures modulate optical phase of the probe beam, which is sent to a photorefractive quantum well (PRQW) device and mixed with a reference local oscillator beam by two-wave mixing. The two-wave mixing self-compensates mechanical disturbances to maintain the quadrature condition with a compensation rate higher than a kHz. Phase modulation caused by protein structures on the spinning disk have frequencies higher than the compensation rate and can be read out by a photodetector. For further details of the AO-class, see U.S. patent application Ser. No. 10/726,772 filed Dec. 3, 2003 entitled "Adaptive Interferometric Multi-Analyte High-Speed Biosensor," previously incorporated by reference herein in its entirety.

A third exemplary quadrature detection class in accordance with the present teachings is the phase-contrast class ("PC-class"), which is analogous to phase-contrast imaging. It uses a Fourier transform of the light diffracted by a protein edge and uses a spilt detector at the Fourier plane to detect intensity shifts at two opposite quadrature angles. The PC-class of quadrature interferometric detection is discussed in U.S. utility application Ser. No. 11/345,462 filed Feb. 1, 2006 and entitled "Method and Apparatus for Phase Contrast Quadrature Interferometric Detection of an Immunoassay," previously incorporated herein by reference.

Another quadrature detection class in accordance with the present teachings is the in-line quadrature class, which is based on the quadrature interference of light reflected from a top $SiO_2$ surface of a biological compact disk substrate and from the bottom silicon surface of the substrate. The phase difference of these two beams is set by the oxide thickness. When the oxide thickness is $\lambda/8$ or $3\lambda/8$, the two beams are in quadrature. The presence of protein scatters the incident beam and adds an optical phase shift, which is then converted to a far-field intensity shift. The intensity shift not only depends on the quadrature interference, but also on the surface electric field strength, and the actual protein signal is a combination of these two factors. The in-line class of quadrature interferometric detection is further disclosed in U.S. utility application Ser. No. 11/675,359 filed Feb. 15, 2007 and entitled "In Line Quadrature and Anti-Reflection Enhanced Phase Quadrature Interferometric Detection," the disclosure of which is incorporated in its entirety by this reference.

The present invention utilizes dielectric structures to generate larger electric fields at the location of the biolayer to be detected. The larger fields produce stronger optical interaction and stronger signals. Methods to produce large fields include multilayer dielectric stacks that may be composed of a single layer on a substrate, or multiple layers on a substrate. In addition to larger electric fields, the present invention also combines the in-phase and conjugate response of the resonance to form a signal that tracks the modulus of the response even in the event that the substrate or layers may not be uniform, making the detection robust to operating point drift.

The biological compact disks of the present invention are sensitive detection platforms that detect immobilized biomolecules on the surface of a spinning disk by using high-speed and self-referencing quadrature laser interferometry. In contrast to static interferometric detection techniques, the present detection platforms are directed to spinning-disk interferometric techniques. These detection platforms have the advantage of operating faraway from 1/f system noise, as well as have a 40 dB per octave slope, which reduces the detection noise floor by more than 50 dB.

To prepare the biological compact disks of the present invention, soft lithography inkpad stamping processes can be used [see for instance, the processes described in U.S. patent application Ser. No. 10/726,772 and U.S. patent application Ser. No. 11/743,913, the disclosures of which are incorporated by reference herein in their entirety; see also, Bietsch, A. and B. Michel, *Conformal contact and pattern stability of stamps used for soft lithography*. J. Appl. Phys., 2000, Vol. 88, p. 4310-4318, and Hu, J., et al., *Using soft lithography to fabricate GaAs/AlGaAs heterostructue field effect transistors*. Appl. Phys. Lett., 1997, Vol. 71, p. 2020-2022]. According to certain aspects of the present invention, patterns of immobilized molecules (antibodies or DNA oligonucleotides) are printed directly onto the disks using a rubber (PDMS) stamp, in which each annular track is composed of on/off repeated segments of antibodies interspersed by bare substrate. The interferometric signal is therefore a difference signal modulated at high frequency by the spin of the disk. More particularly, to detect a bound analyte, a set of control tracks are placed on the disk by applying dual tracks of antibodies thereon (i.e., one antibody that binds to the prepared analyte and another that does not bind to the analyte). The difference between the interferometric signals on the test track and the control track provides the detection signal (specific-to-nonspecific binding).

An exemplary illustration of a spinning-disk self-referencing interferometric laser scanning detection system in accordance with the present invention is depicted in FIG. 1 and labeled generally with reference numeral 100. According to this system 100, the beam 102 from a laser is focused perpendicularly to the surface 104 of a spinning disk 106. Target molecules 108 (such as antibodies for instance) are immobilized on the disk 106. The disk 106 is a resonant substrate that maximizes the electric field of the laser at the surface 104 of the disk where the biolayer or molecules are located. The quadrature condition that is set up by the disk structure converts the phase modulation from the molecules, traversing through the focused beam 116, into intensity modulation that is detected when the reflected light is directed to a photodetector (shown by arrow 110) by the beamsplitter 112.

The detector is configured to detect the modulus of the resonant response. Linearly-responding systems always have two orthogonal responses that are called in-phase and conjugate responses. In previous disclosures discussing the detection of biological compact disks, these responses have been detected separately by adjusting the photodetection configuration or the substrate structure to maximize one while minimizing the other. In accordance with the present detection methods, two detection systems respond separately to the two conjugate channels and then combine them into a single signal that is the modulus of the combined response. This modulus is more robust to drifts in the detector signals or in the properties of the biological compact disk substrate and presents a superior detection mode. An exemplary embodiment of this modulus detection is a segmented photodetector that can measure the differential (left-right or up-down) phase contrast intensity channel and the in-line intensity channel simultaneously, and it is the sum of the squares of these signals that represents the modulus-squared, being robust against drift of the system's operating point.

The biological compact disk 106 is mounted to a spin motor (not shown), which is capable of spinning the disk 106 at various user-defined speeds, such as, for instance, at speeds about 10 Hz to about 100 Hz, and in increments of about 20 Hz. The disk 106 includes concentric tracks (only one track 114 is shown in FIG. 1) of alternating regions or targets of analyzer molecules and reference blanks (shown as interferometric elements 108). While the targets are configured to bind various analytes, the reference blanks are configured to bypass such analyte binding. As the disk 106 spins, a laser sweeps across the targets and reference blanks 108 with a duty cycle of approximately 50%. As nominal values, a typical track 114 may have spot sizes of about 5-10 microns (larger than the beam waist of the focused laser 116) with about 5,000-10,000 spots in a single track at a radius of 1 centimeter. Successive tracks (on a multi-analyte disk) may be spaced by about 5-10 microns apart. For instance, with a 5-micron pitch, a typical disk can hold 10,000 tracks and 100 million spots. Moreover, a single track 114 can contain a single type of analyzer molecule (antibody or cDNA), and the laser can scan over the single track 114 for as long as needed to obtain good data averaging with a small detection bandwidth before moving on to the next track.

In other exemplary detection approaches, the probe laser may be split into two parallel beams that simultaneously illuminate the test and control tracks of the disk. According to this exemplary approach, the dual split beams can be brought through a collection of optics to matched photodetectors that measure and differentiate both signal beams simultaneously to isolate the analyte signal.

In yet other detection approaches, the test tracks and control tracks can be combined into a single track by placing analyzer antibodies in the spots of the disk and non-specific antibodies into the blanks between. This can be achieved through the use of self-limiting soft-lithography, in which the printed antibodies saturate the surface, thereby preventing the immobilization of a second non-specific antibody that is applied to the whole surface such as, for instance, by using avidin-biotin immobilization of Fab (anti-body fragment) [see for example, T. Cass and F. S. Ligler, "Immobilized Biomolecules in Analysis: A Practical Approach," Oxford University Press, 1998].

Figure 2:
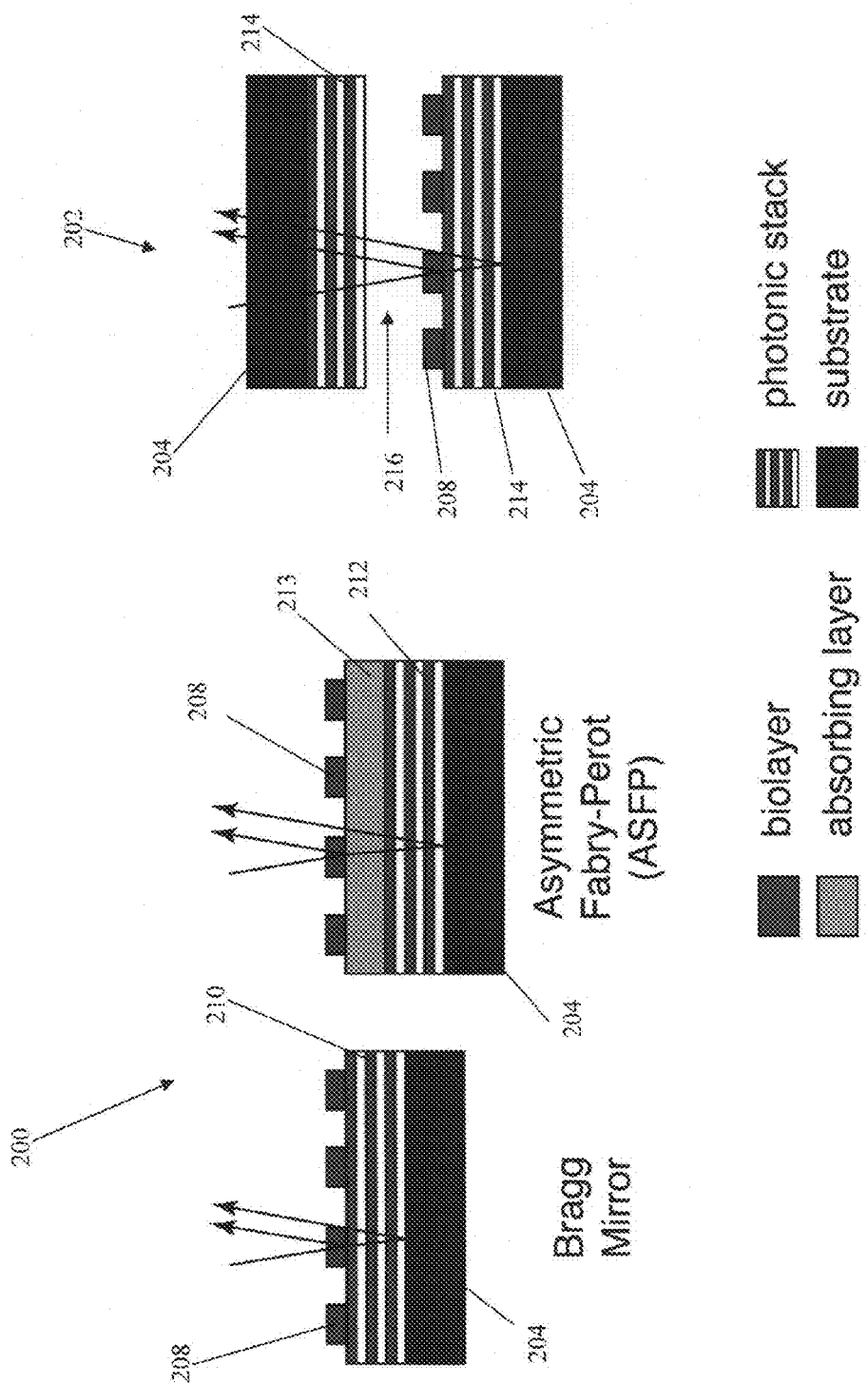
FIG. 2 depicts exemplary photonic cavity structures, including half-cavity and resonant cavity structures in accordance with the present invention.

It should be understood herein that photonic structures in accordance with the present teachings can include any known photonic substrates, such as, but not limited to, anti-reflection coatings, notch filters, bandpass filters and polarizing filters. Furthermore, these substrates can be used either in reflection or transmission applications and can include 2-D and 3-D photonic lattice effects. Two exemplary photonic structures in accordance with the present teachings are shown in FIG. 2. These structures include half cavity structures 200 and resonant cavity structures 202. The half cavity structures 200 consist of a single photonic substrate 204 having a biolayer 208 immobilized thereto. The substrate 204 may be either a simple Bragg dielectric stack 210, or a semiconductor asymmetric Fabry-Perot (ASFP) structure 212 in which an absorbing layer 213 is GaAs and absorbs wavelengths near 840 nm. Resonant cavity structures 202, on the other hand, are composed of two Bragg stacks 214 facing each other and with an air-gap 216 of about 5-10 microns positioned therebetween. Moreover, a biolayer 208 is immobilized on one of the two photonic stacks 214 and a serum with a target antigen/toxin is flowed through the gap 216.

As will be explained below, resonant cavity performance in accordance with the present invention is influenced by the uniformity of spacing between the upper and lower photonic stacks. For instance, in one exemplary illustration, a 4-inch diameter disk with a stack reflectance of 90% has a spacing variation smaller than about 12.5 nm for a gap of 5 microns. As such, it is possible to maintain a small variation around a circumferential track at a fixed radius from the spin axis by using photoresist posts capable of maintaining the separation between the upper and lower stacks. According to this aspect of the invention, the photoresist is spun onto the wafers at high angular velocity, and although there can be nearly a micron variation in resist thickness center-to-rim, the variation in resist thickness around a circumferential track can be small (e.g., down to tens of nanometers) because of the cylindrical symmetry of the spinning process. Such an approach can be used for patterning a distributed array of resist pillars on one of the two stacks, while printing the antibody arrays on the other stack, and then bringing the two stacks together to rest on the pillars and form the cavity.

As described above, the photonic approach to self-referencing interferometry uses multi-wave interference in dielectric substrates. Dielectric resonators in accordance with the present invention include, but are not limited to, dielectric stacks, dielectric cavities (e.g., linear cavities, 1D, Fabry-Perot), planar cavities (e.g., 2D, whispering gallery modes) and volumetric cavities (e.g., 3D, glass beads, gold spheres, fluorophore droplets). Selective antibodies (selective to specific antigens/toxins/proteins) are immobilized in annular tracks on the surface of at least one of the substrates, providing an index change that is converted to an intensity change upon binding of an antigen when the interferometer is in quadrature (i.e., at the edges of the reflectance-bands (stopbands) for the half cavities and at the edges of the resonances in the resonant cavities).

According to one aspect of the present invention, the signal-to-noise ratio for interferometric detection on a reflective photonic stack in the shot-noise-limited regime is:

$$\frac{S}{N} = \frac{i_s^2}{i_d e B} = \frac{P_0}{h\nu B}\eta_Q \frac{\Delta R^2}{R}$$

wherein $i_s$ represents the modulated signal, $i_d$ represents the total detector current, B is the noise-equivalent detection bandwidth, $\eta_Q$ is the detector quantum efficiency, $P_0$ is the optical power incident on the interferometer, $\Delta R$ is the change in reflectance caused by the biolayer and R is the reflectance of the interferometer at the operating wavelength.

As used herein, interferometric gain $g(\lambda)$ refers to the ratio of the relative intensity change in the photonic interferometer divided by the intensity change from a conventional Mach-Zender interferometer when a biolayer of thickness d and relative index $\Delta n$ is introduced in the sample arm of the interferometer. The response of the reflection interferometer in terms of $g(\lambda)$ is given as:

$$\Delta R = g(\lambda) R \frac{2\pi}{\lambda} \Delta nd \quad (1)$$

The gain for half-cavities is typically close to unity, while for resonant cavities, the gain can approach many tens or hundreds, depending on the cavity finesse. The signal-to-noise may be written in terms of gain as:

$$\frac{S}{N} = \frac{i_s^2}{i_d e B} = \frac{P_0 \eta_Q R}{h\nu B} \left( g(\lambda) \frac{2\pi}{\lambda} \Delta nd \right)^2 \quad (2)$$

This ratio depends linearly on the reflectance R.

For sub-monolayer coverage of a macromolecule, the effective $\Delta nd$ product of the biolayer may be defined as a mean value given by:

$$\Delta nd = \Delta n_m V_m \sigma \quad (3)$$

where $\Delta n_m$ is the effective molecular refractive index difference for isolated molecules on the surface, $V_m$ is the molecular volume, and $\sigma$ is the number density per area.

For a minimum detectable signal, a signal-to-noise ratio equal to about 2 may be provided to give the minimum number of detectable molecules as:

$$N_{min} = \sqrt{\frac{\hbar c \lambda R B}{4\pi P_0 \eta_Q}} \frac{w_0^2}{g \Delta n V_m} \quad (4)$$

For values characteristic of spinning disk experiments of $P_0$=1 mW, B=1 kHz, $\eta_Q$=0.7, $w_0$=20 μm, $\Delta n$=0.3, g=1, $\lambda$=800 nm, R=0.5 and $V_m$=500 nm$^3$, this gives a noise-equivalent molecular detection sensitivity of approximately 100 molecules per focal spot and $10^5$ molecules per track at 1024 spots per track. On a disk with 10,000 concentric tracks, for example, the total molecular detection sensitivity per disk is about 1 femtomoles.

At powers of 100 mW and a detection bandwidth of down to 10 Hz, or for g=100, the sensitivity is found to be about 1 molecule per spot. This is because, unlike single-molecule optical detection schemes that use fluorescence techniques having small photon fluxes (see for example, T. Basche, *Single-molecule optical detection, imaging and spectroscopy*: Cambridge: VCH, 1997], the high photon fluxes and high detection rates associated with the present spinning disks make it possible to detect these small numbers interferometrically.

Exemplary substrates for half-cavity photonic structures according to the present invention include non-absorbing dielectric layers and absorbing dielectric layers. Non-absorbing dielectric layers include Bragg reflectors, while absorbing dielectric layers include asymmetric Fabry-Perot structures.

Bragg stop-band-edge quadrature configurations, according to exemplary embodiments of the present invention, include a single immobilized layer of antibody on the surface of a Bragg dielectric stack (mirrors). Regarding the structure of the Bragg dielectric stack configurations, these structures comprise 1-D photonic bandgap materials that prevent the penetration (to significant depth) of incident electromagnetic modes. Moreover, at the edges of the stop-band, near the 50% intensity wavelength, the standing wave in the incident half-space has neither a node nor an anti-node at the surface, but instead is in the condition of quadrature with a π/2 relative phase. This structure is in contrast to configurations in which the node occurs at the surface of a metallic reflecting layer, or the antinode occurs at wavelengths near the center of the stop-band. For this reason, the presence or absence of a small layer of relative index Δn produces a notable change in the reflectance ΔR.

Figure 3A:
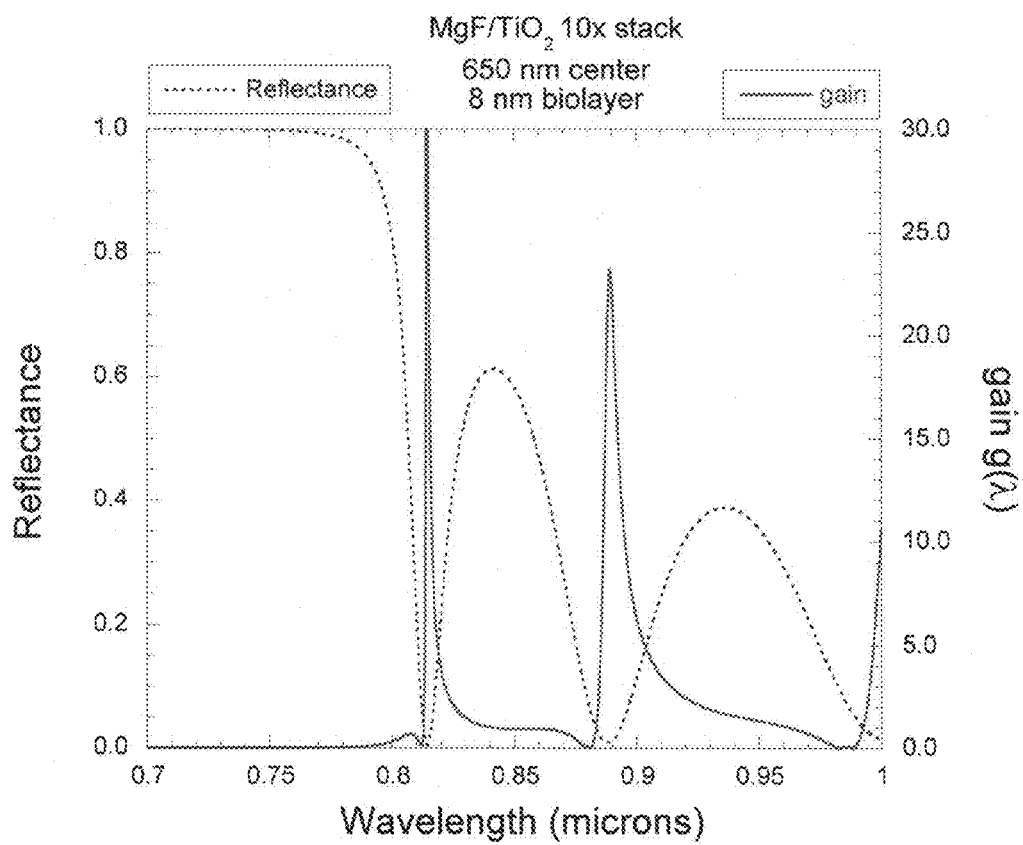
FIG. 3a depicts reflectance and interferometric gain of a biolayer on a dielectric 10× MgF/TiO$_2$ Bragg stack with a center wavelength of 650 nm in accordance with the present invention.

FIG. 3a depicts an illustrative interferometric gain from Equation (1) above for a 10× MgF/TiO$_2$ dielectric quarter-wave stack with a center wavelength of 650 nm in response to an 8 nm biolayer with a refractive index of n=1.35, calculated using a transfer-matrix approach [see for example, D. D. Nolte and K. M. Kwolek, "Diffraction from a Short-Cavity Fabry-Perot: Applications to Photorefractive Quantum Wells," *Opt. Commun.*, vol. 115, pp. 606-616, 1995]. The reflectance of the stack is also shown. The long-wavelength edge of the reflectance-band (stop-band) occurs around 800 nm, where the dR/dλ slope is steepest. In the side bands, the gain is resonant at several wavelengths in the region of the sidelobes and at conditions of quadrature.

According to one aspect herein, the present invention is also directed to the interferometric detection of antibody binding using high-speed spinning-disk interferometry in the Bragg side band of a dielectric disk in a biological compact disk format, enabling 4-channel detection through independent phase contrast, in-line, light scattering and fluorescence channels. In accordance with this aspect of the present invention, the biological compact disks are high-speed label-free immunoassays based on stable common-path interferometry on a spinning disk [see for example, David D. Nolte and Fred E. Regnier, "Spinning-Disk Interferometry The BioCD," *Optics & Photonics News*, pp. 42-53, October, 2004]. High-speed sampling on these disks provides a 50 dB signal-to-noise advantage over static interferometric biosensors. Previous biological compact disk classes have made the distinction between micro-diffraction [see for example, M. M. Varma and D. D. Nolte, "Spinning-disk self-referencing interferometry of antigen-antibody recognition," *OPTICS LETTERS*, Vol. 29, No. 9, pp. 950-953, 2004], phase contrast and in-line interferometric quadratures. According to one aspect of the present teachings, phase-contrast and in-line quadratures are unified into a single interferometric detection class by the use of the spectral side-lobes of a Bragg dielectric stack. Phase and amplitude modulation caused by molecular recognition of antigen by antibodies immobilized on top of the stack trade off against each other as a function of wavelength on the edge of the stop-band. Combining the interferometric detection channels with conventional light-scattering and fluorescence channels introduces a versatile new biological compact disk platform for sensitive analytical bioassay applications. The theoretical relationships among the Bragg stack's structure, in-line and phase contrast signal intensities is also outlined in these teachings. The theory can guide the design of the desired structure, which maximizes the sensitivity of in-line or phase contrast (PC) channel detection. It is also shown that by combining both channels in quadrature, the joint signal is insensitive to drifting properties of the substrate, incident angle or wavelength [see for example, X. Wang, M. Zhao, and D. D. Nolte, "Common-path interferometric detection of protein monolayer on the BioCD," Appl. Opt. 46, 7836-7849 (November 2007), the disclosure of which is incorporated in its entirety herein by this reference].

An exemplary illustration of the above-described unified interferometric detection process can be seen with reference to FIGS. 4a-4d. Here, on the same region of protein pattern, whose thickness is approximately a monolayer or about 1~4 nm, imaging is illuminated at 488 nm and is performed simultaneously with four channels—i.e., (a) light scattering imaging, (b) fluorescence imaging, (c) phase contrast interferometry imaging, and (d) in-line interferometry imaging. As can be seen in FIGS. 4a-4d, all channels provide complimentary information, and all channels except the light scattering show strong signals.

In the theoretical derivation of common-path interferometric detection of protein, both interference and diffraction upon reflection from the substrate and detection in the Fourier plane are considered. This is started with a reflecting planar substrate having a complex reflection coefficient (r), which carries a protein layer of thickness h(x). No explicit boundary conditions are assumed for the substrate other than the reflected amplitude and phase. The normalized two-dimensional intensity distribution of the incident Gaussian beam is:

$$I(\rho) = \frac{1}{2\pi w_0^2} e^{-\rho^2/2w_0^2} \quad (5)$$

where $\rho^2 = x^2 + y^2$, with the corresponding dimensionless electric field:

$$g(\rho) = g(x, y) = \frac{1}{\sqrt{2\pi}\, w_0} e^{-\rho^2/4w_0^2} \quad (6)$$

and two-dimensional Fourier transform:

$$G(k_x, k_y) = 2\sqrt{2\pi}\, w_0 e^{-w_0^2 k^2} \quad (7)$$

The two-dimensional diffraction problem is considered in the Fraunhofer regime. The reflected near-field is:

$$E(x, y) = r'(x, y)g(x, y) = (r + iP(r)\delta)g(x, y) \quad (8)$$
$$= \left(r + iP(r)\frac{2\pi n_p h(x - vt, y)\cos\theta_0}{\lambda}\right)g(x, y)$$
$$= r(1 + iQ(r)h(x - vt, y))g(x, y)$$

Here, $$Q(r) = \frac{P(r)}{r}\frac{2\pi n_p \cos\theta_0}{\lambda} \quad (9)$$
$$= \left(\frac{(r_p - r)(1 - rr_p)}{r(1 - r_p^2)} + \frac{\tan\theta_p}{\tan\theta_0}\right)\frac{4\pi n_p \cos\theta_0}{\lambda}$$

where $\theta_0$ is the incident angle, $\theta_p$ is the angle inside the protein layer, and where the surface topology, including the motion of the disk, is contained in the real-valued height function $h(x-vt, y)$.

The far field is:

$$E(k_x, k_y) = r(G(k_x, k_y) + iQ(r)FT[g(x, y)h(x - vt, y)]) \quad (10)$$
$$= r(G(k_x, k_y) + iQ(r)H(k, t))$$

where FT stands for Fourier transform and the transformed function is:

$$H(k, t) = FT[g(x, y)h(x - vt, y)] \quad (11)$$

For a nodal boundary condition, where r=−1, the value of Q(r) in equation (9) is Q(r)=0. This has the initially surprising consequence that a biofilm on a nodal surface causes no amplitude and no phase shift and is hence effectively "invisible." This is because on a perfect nodal surface, the electric field is zero and hence there is no molecular scattering that is the origin of phase shifts and refractive indices. On the other hand, for an ideal anti-nodal surface, where r=1, the phase shift takes on a maximum value. These limiting cases are:

$$Q(r) = \begin{cases} 0 & \text{nodal} \\ \dfrac{4\pi(1 - n_p^2)}{\lambda} & \text{anti-nodal} \end{cases} \quad (12)$$

with general substrates having values between these extremes.

The intensity at the detection (Fourier) plane is:

$$I(k_x, k_y; t) = |r(G(k_x, k_y) + iQ(r)H(k, t))|^2 \quad (13)$$
$$\approx |r|^2(|G(k_x, k_y)|^2 +$$
$$iG(k_x, k_y)[Q(r)H(k, t) - (Q(r))^* H^*(k, t)])$$
$$= |r|^2(|G(k_x, k_y)|^2 + 2G(k_x, k_y)\text{Im}(Q(r)H(k, t)))$$

The detected photocurrent is obtained by integrating Equation (13) over the Fourier-plane detector response function R(k) that can be controlled by appropriate apertures or split detectors. The normalized photocurrent is:

$$i_d(t) = \int_{-\infty}^{\infty} R(k_x, k_y)I(k_x, k_y; t) d^2k \quad (14)$$

Restricting the problem to the one-dimensional case, the differential phase-contrast signal in the x-direction is obtained using a split detector with inversion and summation circuits. This is the differential phase contrast channel with the photocurrent $$i_d(t) = \int_{-\infty}^{0} I(k_x, t) dk_x - \int_{0}^{\infty} I(k_x, t) dk_x \quad (15)$$
$$= 4|r|^2 \int_{0}^{\infty} G(k_x)\text{Im}(Q(r)H(k_x, t))_{odd}\, dk_x$$

where $R(k_x)$ is now a step function at $k_x=0$, and the subscript "odd" refers to only the odd functions of Im $(Q(r)H(k,t))$ because G(k) is already an even function of k.

For the in-line channel, $R(k_x, k_y)$ is a constant function, and the photocurrent is:

$$i_d(t) = \int_{-\infty}^{\infty} I(k_x; t) dk_x \quad (16)$$
$$= I_0|r|^2 + 4|r|^2 \int_{-\infty}^{\infty} G(k_x)\text{Im}(Q(r)H(k_x, t))_{even}\, dk_x$$

The two different detector output currents are now proportional to the quantities:

$$i_d^{DPC} = \frac{|r|^2}{2}\phi_{Re}\frac{|g(x)|^2}{|g(0)|^2} \otimes \left[\sigma\frac{dh(x)}{dx}\right] \quad (17)$$

$$i_d^{IL} = \frac{|r|^2}{2}\phi_{Im}\frac{|g(x)|^2}{|g(0)|^2} \otimes [h(x)]$$

which illustrates the contribution from higher-order derivatives, where:

$$\phi_{Re} = \frac{4\pi n_p \cos\theta_0}{\lambda}\left(\text{Re}\left(\frac{(r_p-r)(1-rr_p)}{r(1-r_p^2)}\right) + \frac{\tan\theta_p}{\tan\theta_0}\right) \quad (18)$$

$$\phi_{Im} = \frac{4\pi n_p \cos\theta_0}{\lambda}\text{Im}\left(\frac{(r_p-r)(1-rr_p)}{r(1-r_p^2)}\right) \quad (19)$$

These relations show the clear separation between the two detection channels. Differential phase contrast senses the differential protein height, being most sensitive to slopes and steps, while being insensitive to areas of uniform thickness. The far-field symmetry is antisymmetric, and the phase-contrast sensitivity is maximized when the reflectivity is real and positive (nodal surface). The in-line channel has all the opposite attributes, sensing the direct protein height with a far-field that is symmetric. The in-line channel is maximized when the reflectivity is purely imaginary. One way to achieve a purely imaginary substrate reflectivity is an eighth-wavelength layer (and hence the term 'in-line'), but other more complicated substrate structures can achieve this phase condition as well.

It is also possible to combine both channels in quadrature. The joint signal, or modulus, becomes:

$$i_{joint} = \sqrt{(i_d^{DPC})^2 + (i_d^{IL})^2}$$

Figure 3B:
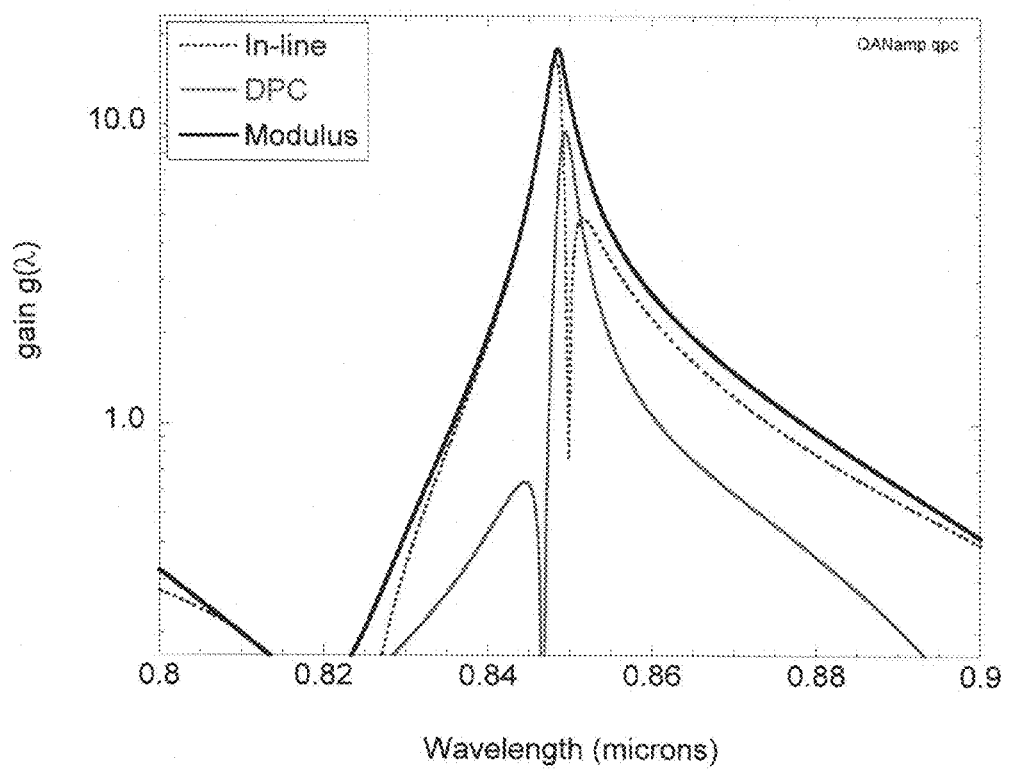
FIG. 3b depicts the in-line and differential phase contrast channel responses of the Bragg stack depicted in FIG. 3a, including the modulus response of the conjugate channels, which shows a broader range of operating wavelength.

This combined signal is much less sensitive to drifts in the substrate properties, or to thickness changes of the substrate, or changes in incident angle or incident wavelength. For instance, the sharp resonances in FIG. 3a would make it difficult to tune the wavelength or the substrate thickness to be directly on-resonance. By considering the modulus of the in-line and differential phase contrast signals, as shown in FIG. 3b, the working wavelength range, and also the working thickness range of the substrate, are extended, thereby relaxing the strict requirement for wavelength and thickness.

Figure 3C:
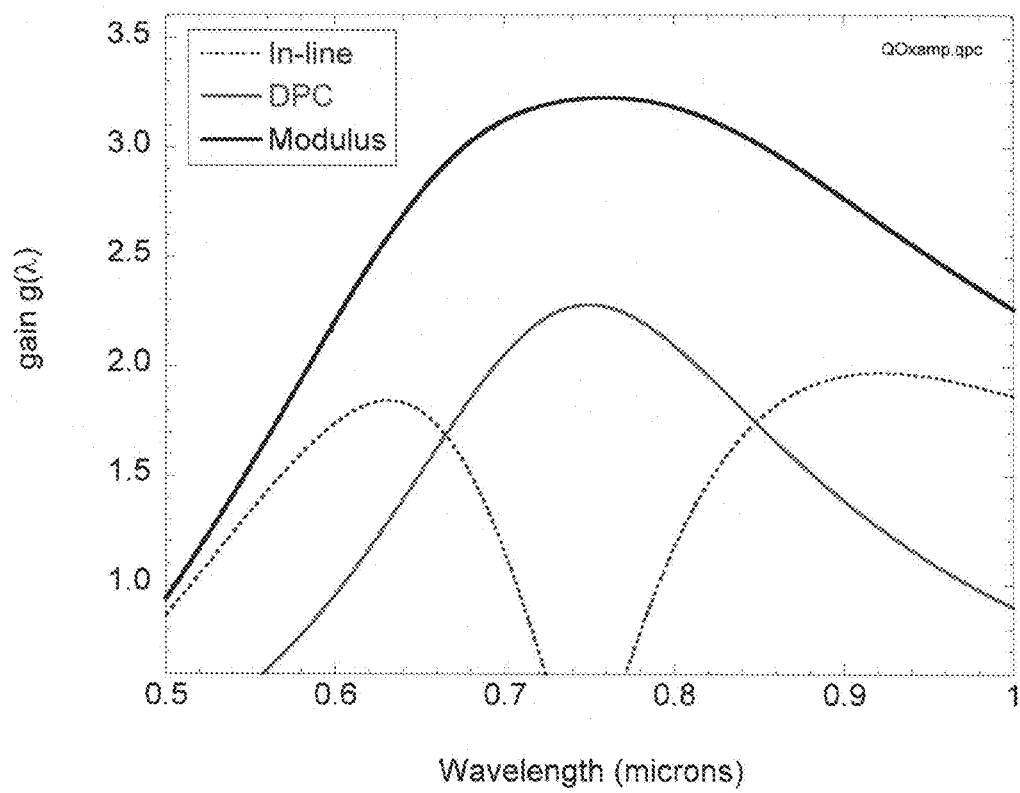
FIG. 3c depicts the in-line and differential phase contrast channel responses of 120 nm thermal oxide on silicon, including the modulus response of the conjugate channels, which shows a broader range of operating wavelength than either channel separately.
Figure 3D:
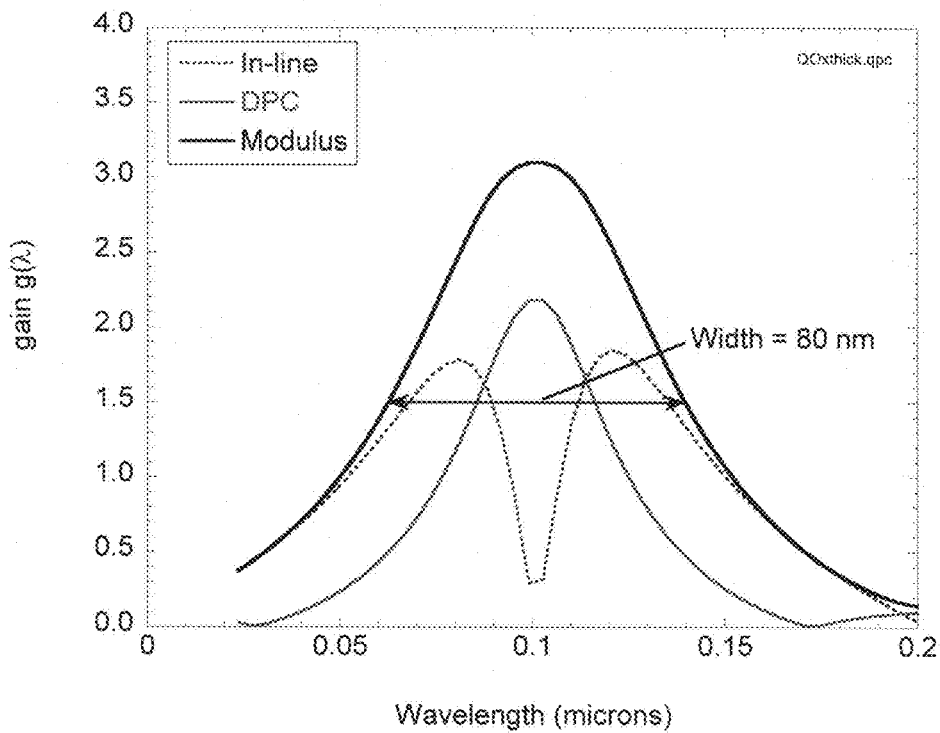
FIG. 3d depicts the in-line and differential phase contrast channel responses of thermal oxide on silicon as a function of oxide thickness at a wavelength of 635 nm, including the modulus response of the conjugate channels, which shows a broader range of operating thickness than either channel separately.
Figure 4A:
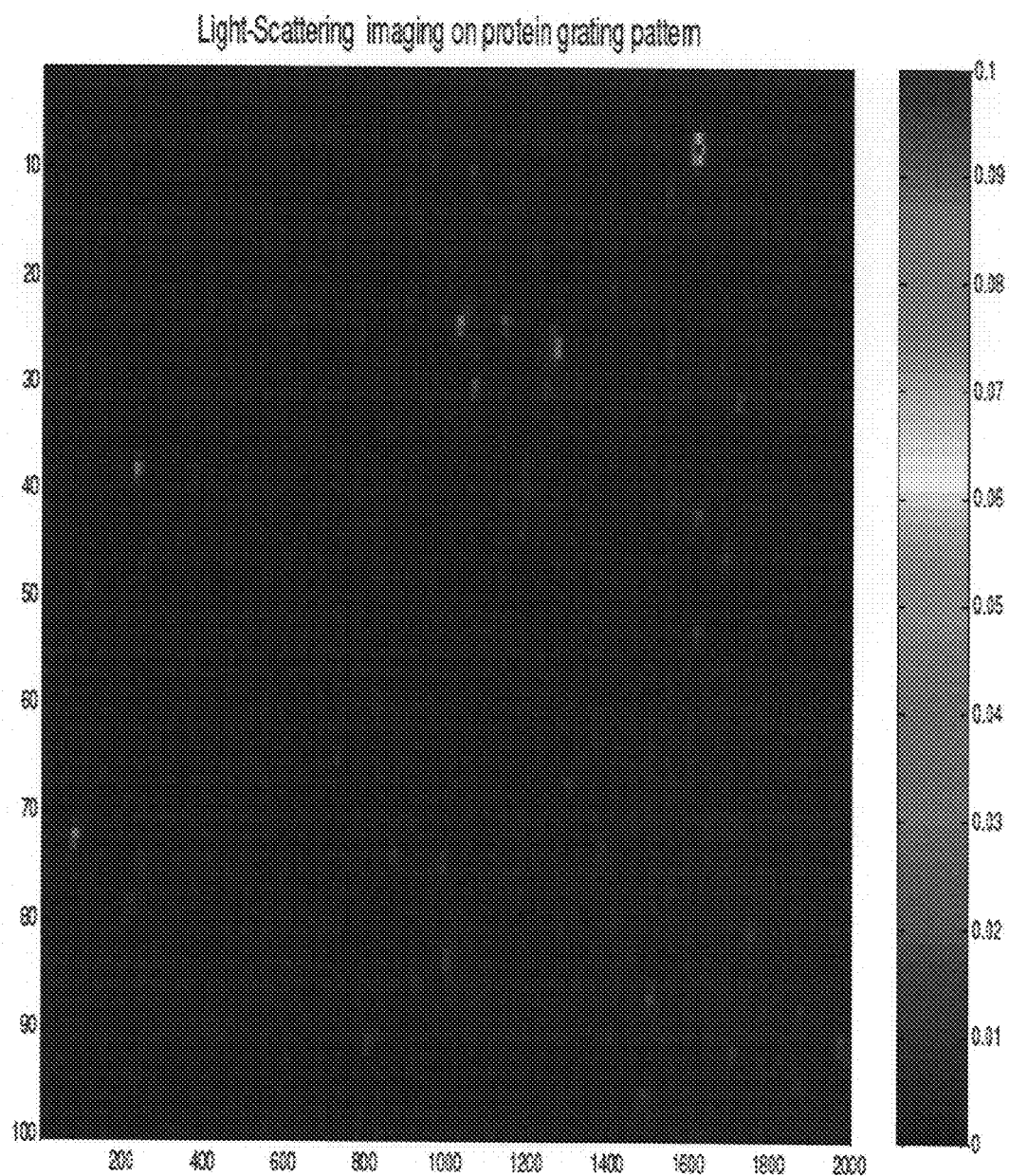
FIG. 4a depicts a protein grating pattern of a biological compact disk imaged by a light-scattering imaging method.
Figure 4B:
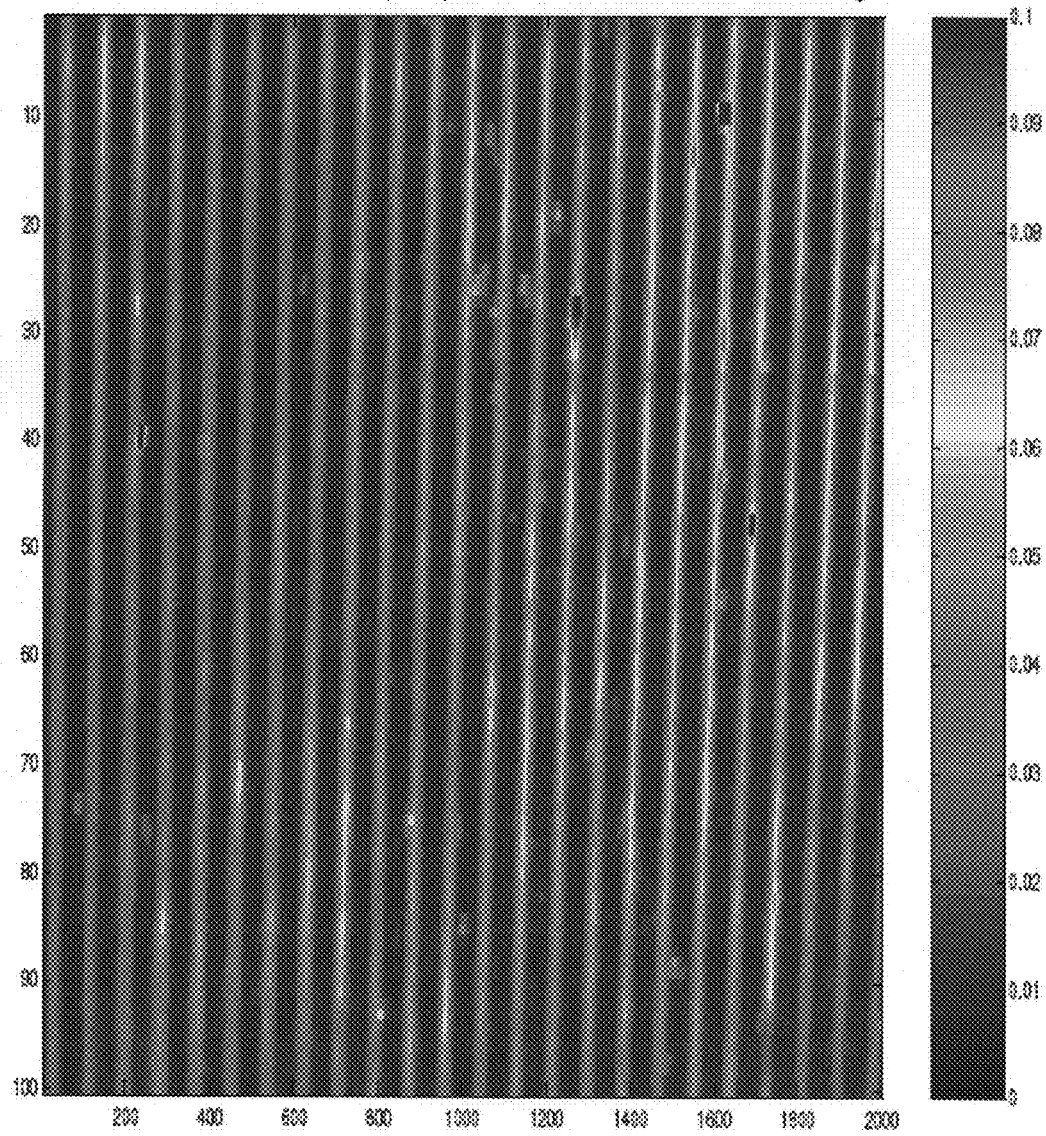
FIG. 4b depicts a protein grating pattern of a biological compact disk imaged by a fluorescence imaging method.
Figure 4E:
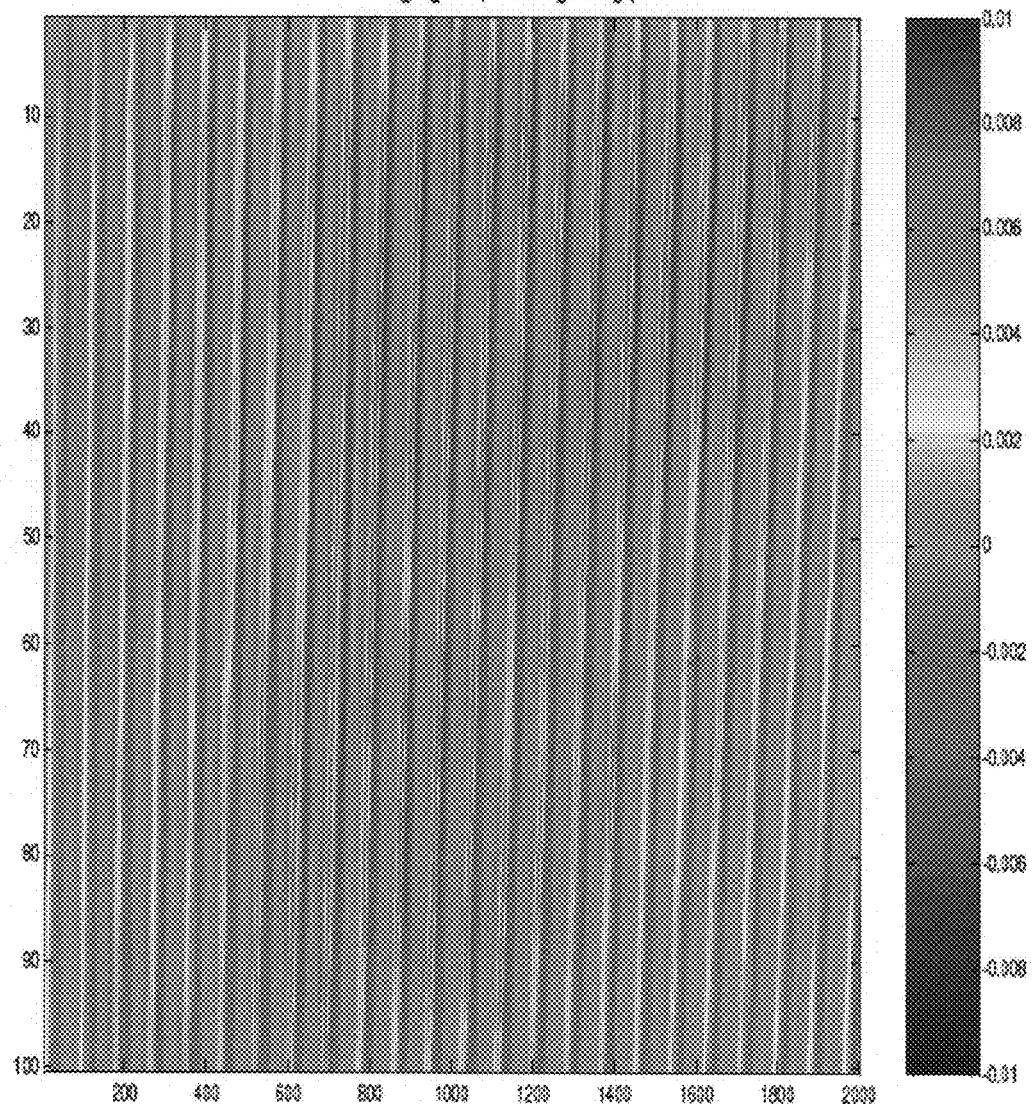
FIG. 4c depicts a protein grating pattern of a biological compact disk imaged by a phase contrast interferometry imaging method.
FIG. 4d depicts a protein grating pattern of a biological compact disk imaged by an in-line interferometry imaging method.
Figure 4D:
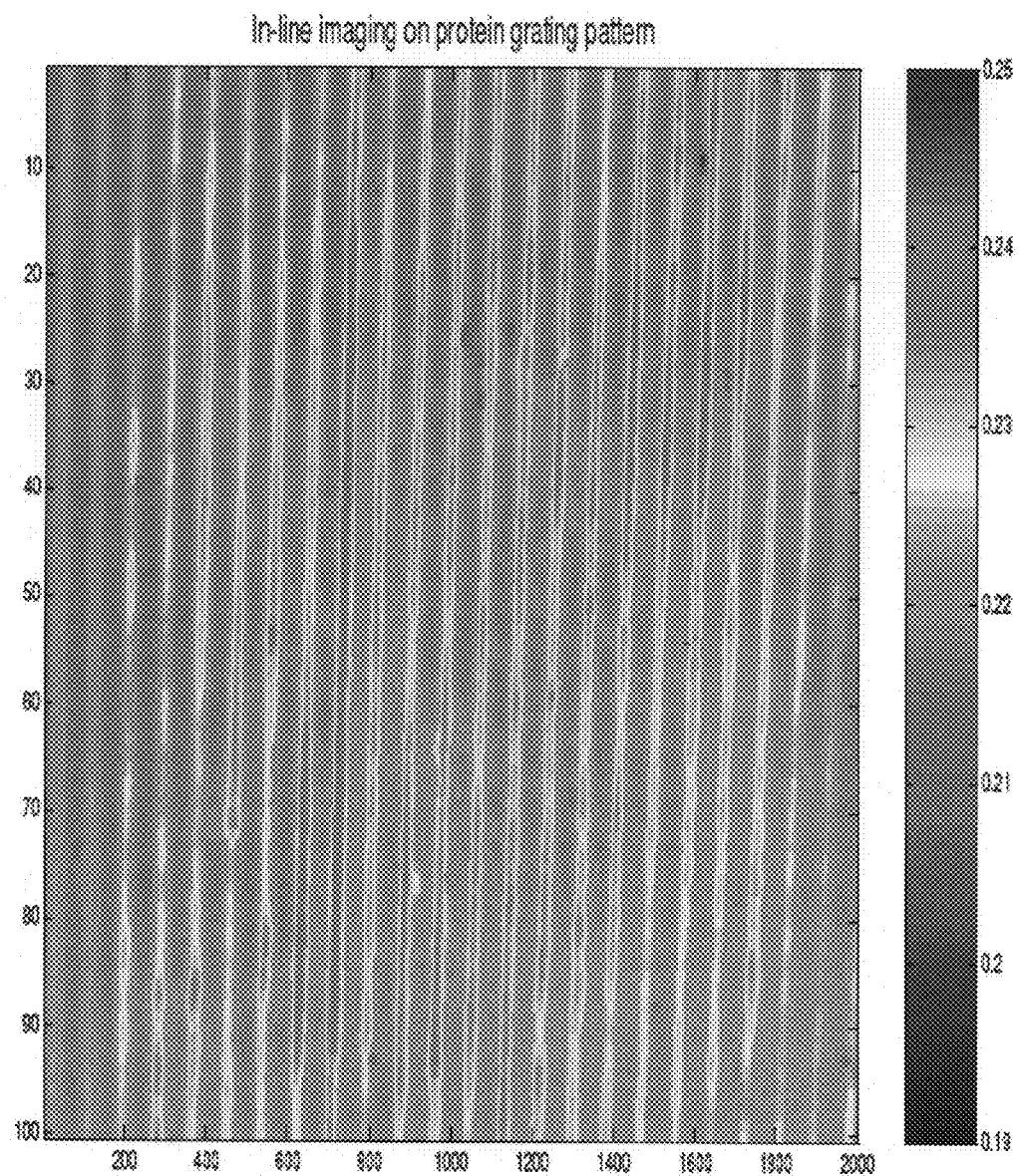

Another example of the modulus signal is shown in FIG. 3c for a thermal oxide on silicon with a thickness of 120 nm probed. The graph shows the in-line and the differential phase contrast response, which both show wavelength dependence. In the case of the in-line signal, it can vary rapidly with both thickness and wavelength when near the resonant condition. The modulus, on the other hand, is broader and varies more slowly with wavelength. The thickness dependence at a wavelength of 635 nm is shown in FIG. 3d. The full-width of the modulus is 80 nm for the oxide thickness, compared to a working width of only about 20 microns for the inline signal near one of its maxima. These results illustrate the improvement in signal robustness that is achieved by working with the modulus of the two-channel signals.

According to one exemplary embodiment herein, the structure of the Bragg stack is comprised of ten repeated layers of $SiO_2$ and $Ta_2O_5$ having a thicknesses of 113.4 nm and 72.2 nm, respectively on a glass substrate. The center reflection wavelength for this stack is 635 nm with a bandwidth of 200 nm. According to this embodiment, the short-wavelength side of the stop-band near 488 nm in the side band region with several wavelength-dependent reflectance maxima and minima is utilized. Antibodies are spatially patterned on the top layer of the Bragg stack using soft lithography or protein spotting. Usually, these protein patterns are monolayered and have a thickness of about 1–4 nm. The phase modulation caused by the immobilized biological molecules is converted into intensity at the detector through either in-line (using symmetric detector function) or phase contrast (using the anti-symmetric detector function) interferometry. Because the Bragg side bands have strong dispersion, phase and amplitude effects are easily converted into each other by changing wavelength or incident angle. Combining both interferometric detection channels into a single detection mode provides versatility and robustness relative to previous separate detection.

Figure 5A:
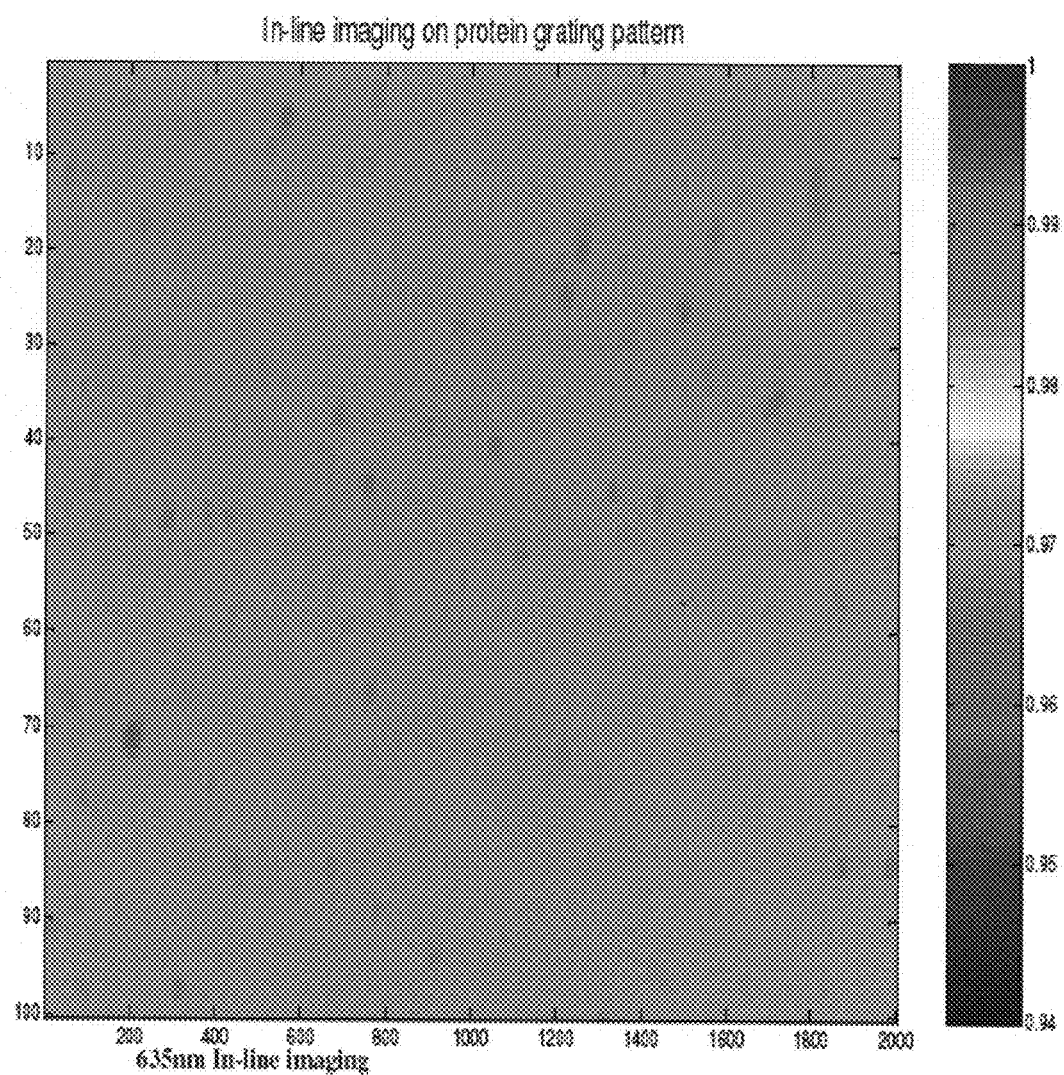
FIG. 5a depicts a protein grating pattern of a biological compact disk imaged by an in-line interferometry imaging method at a wavelength of 635 nm.
Figure 5B:
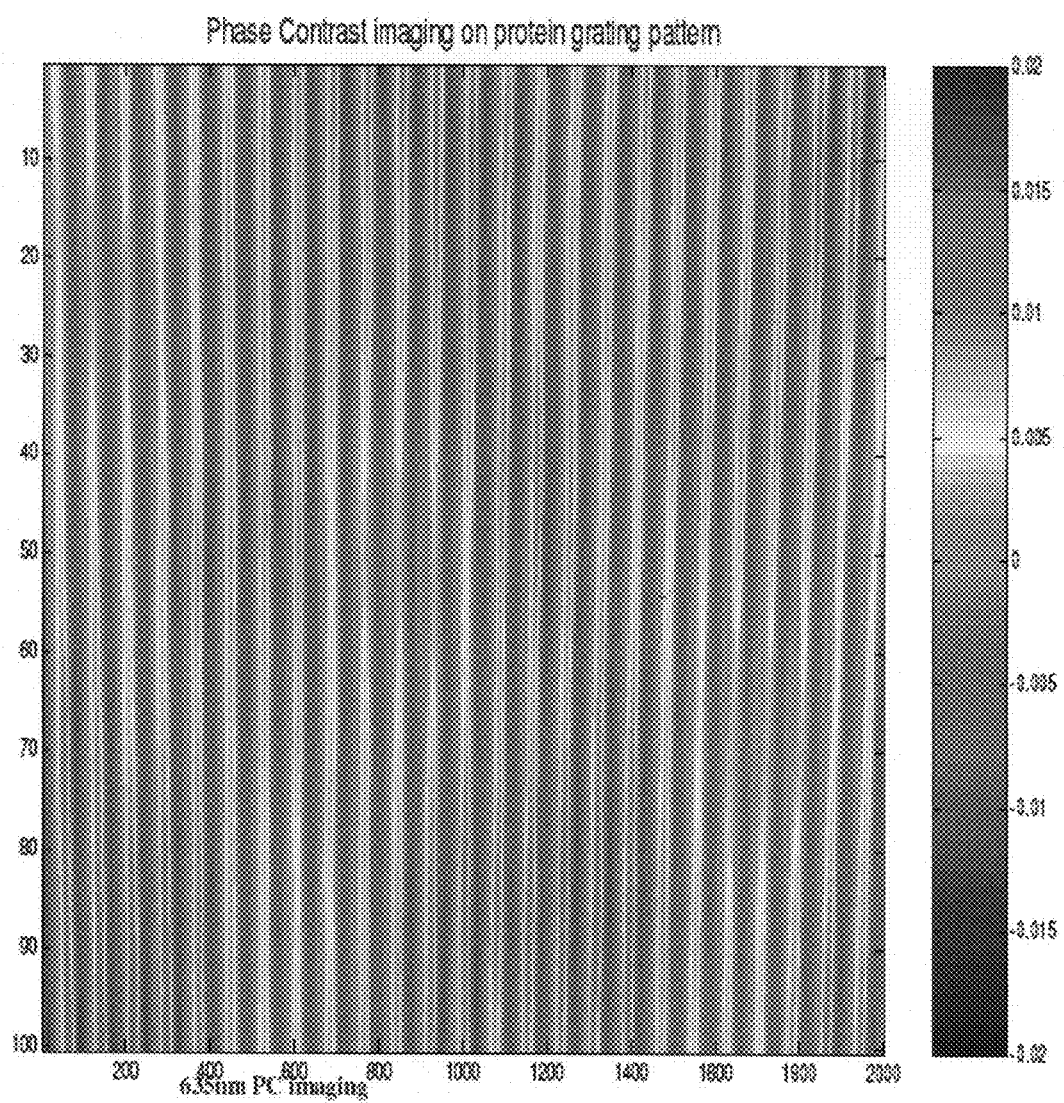
FIG. 5b depicts a protein grating pattern of a biological compact disk imaged by a phase contrast interferometry imaging method at a wavelength of 635 nm.
Figure 5C:
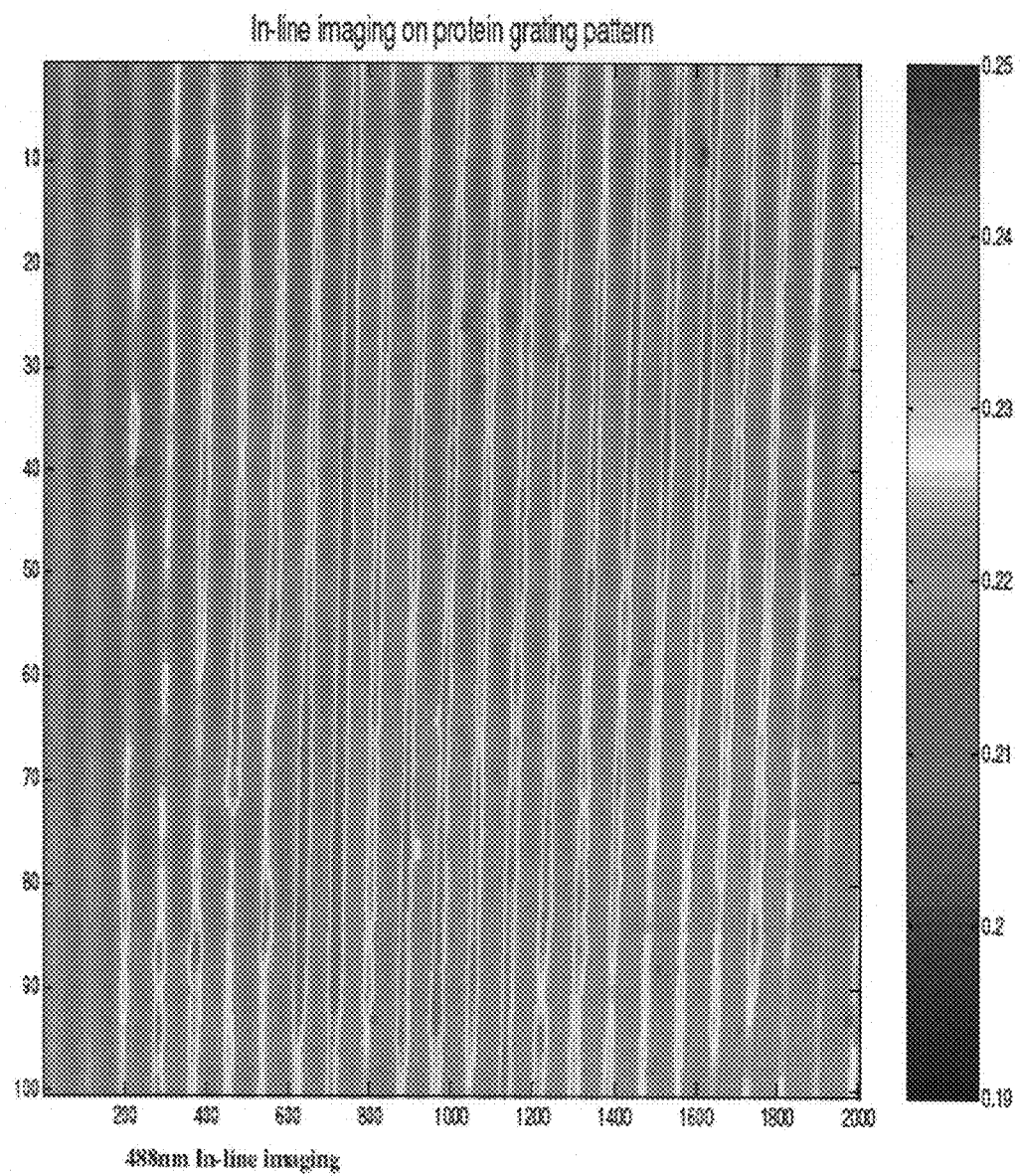
FIG. 5c depicts a protein grating pattern of a biological compact disk imaged by an in-line interferometry imaging method at a wavelength of 488 nm.
Figure 5D:
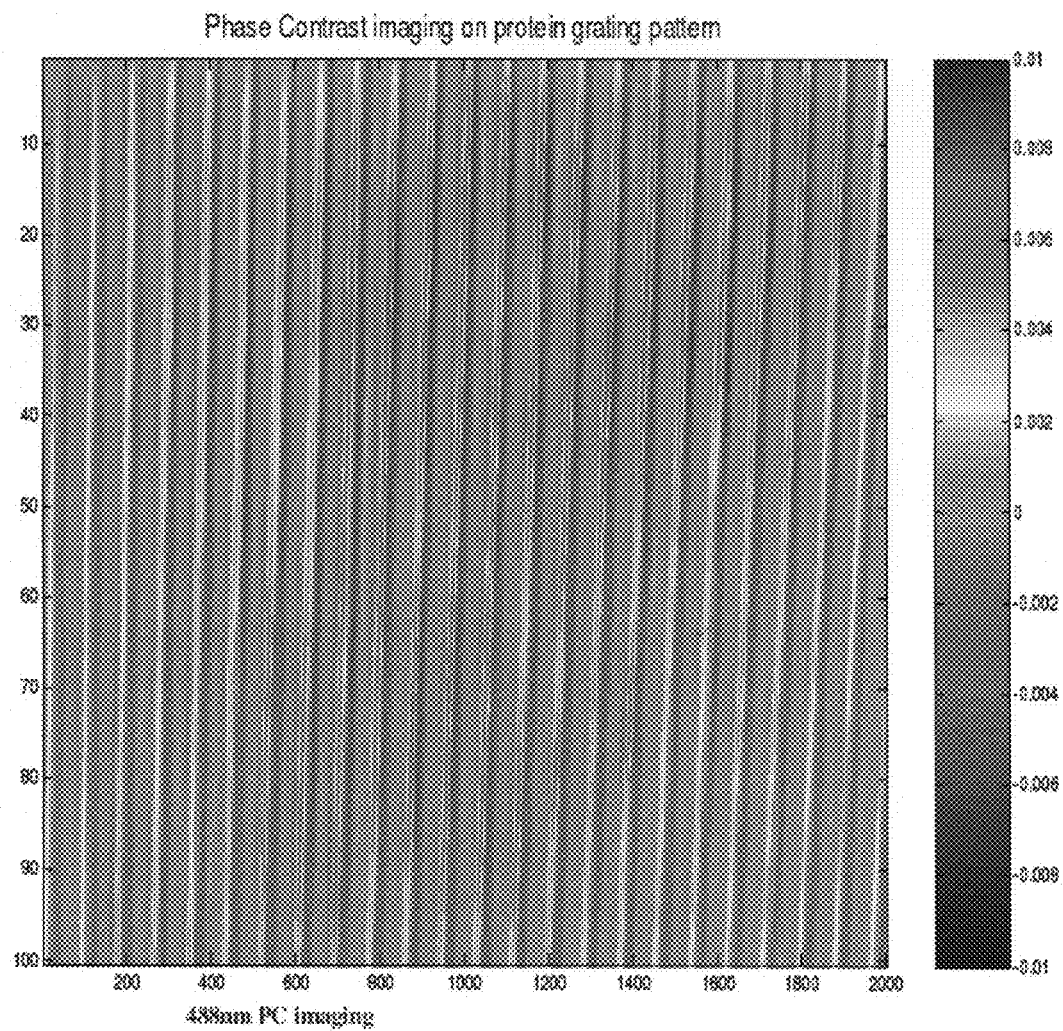
FIG. 5d depicts a protein grating pattern of a biological compact disk imaged by a phase contrast interferometry imaging method at a wavelength of 488 nm.
Figure 5E:
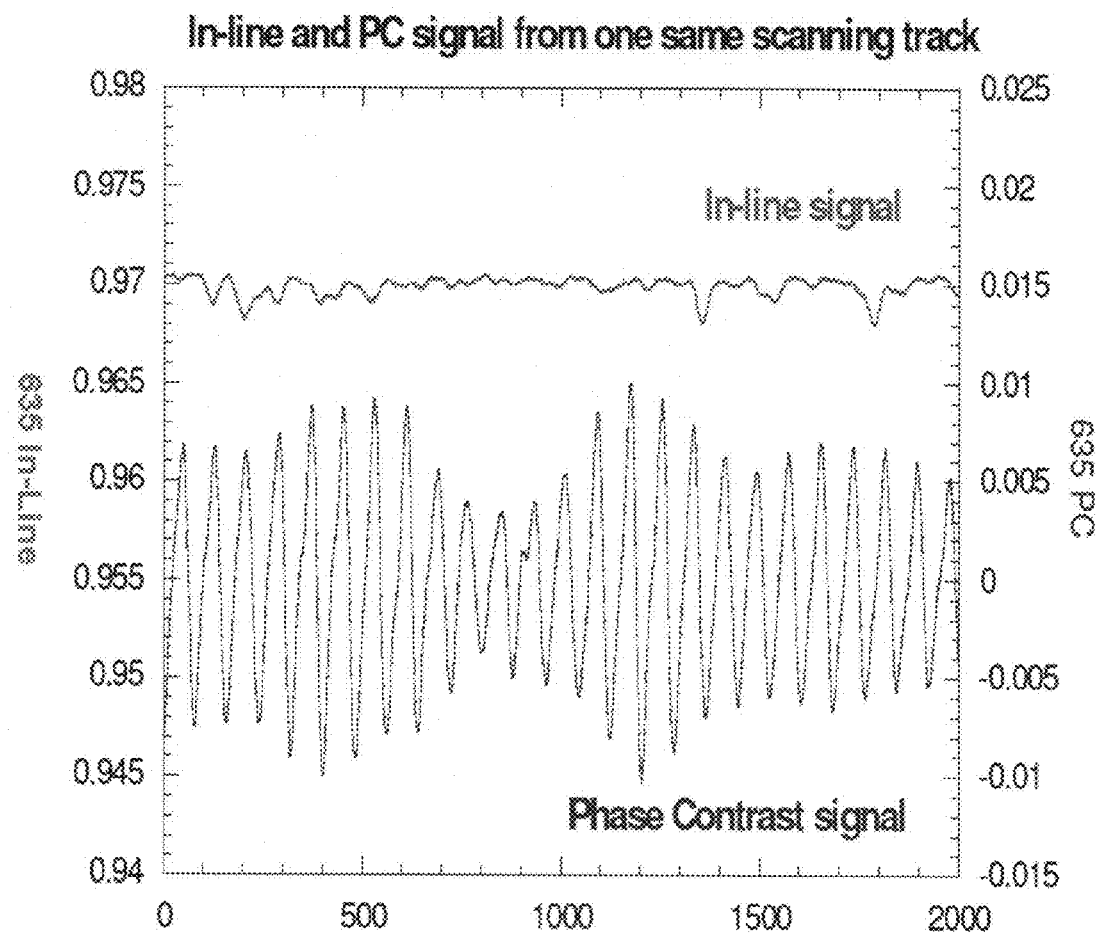
FIG. 5e depicts a graphical representation of in-line and phase contrast interferometry signals from a scanned track of an exemplary biological compact disk at a wavelength of 635 nm.
Figure 5F:
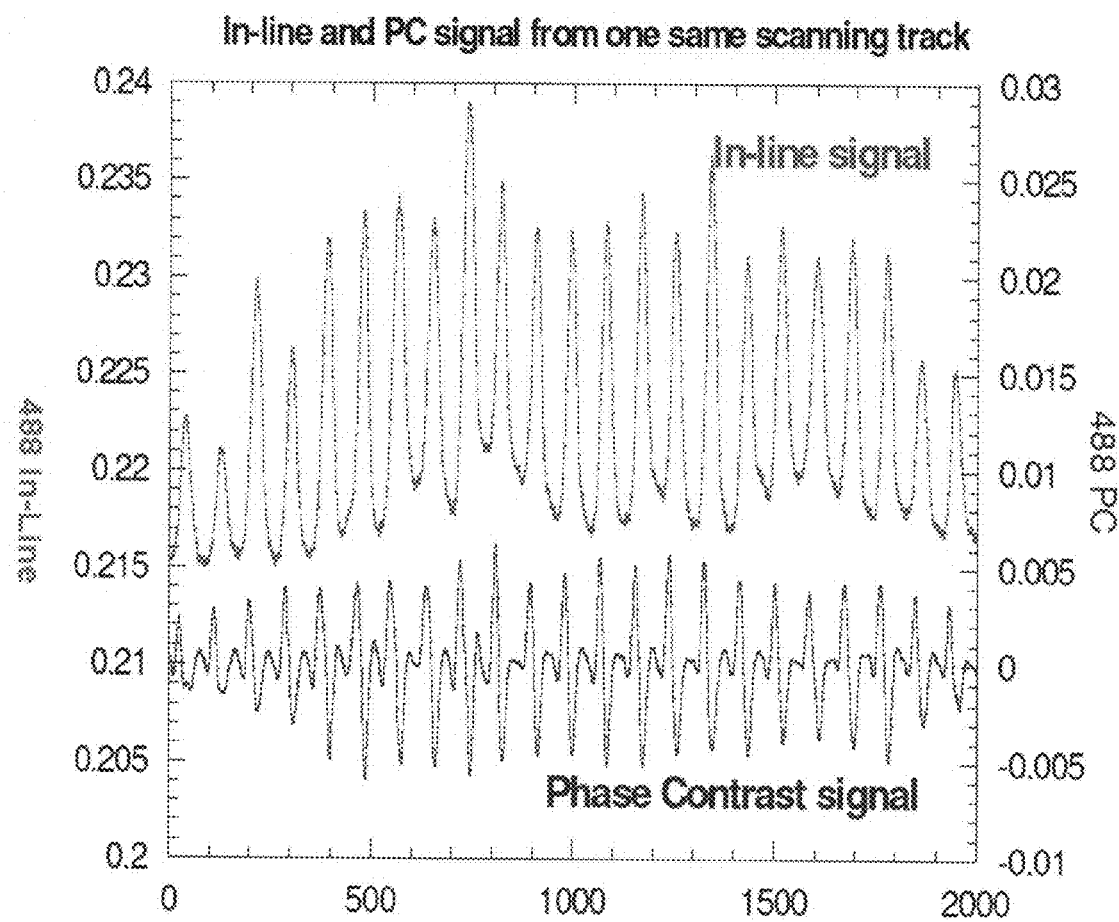
FIG. 5f depicts a graphical representation of in-line and phase contrast interferometry signals from a scanned track of an exemplary biological compact disk at a wavelength of 488 nm.

The wavelength dependence of the detection is illustrated in FIGS. 5e and 5f showing both phase contrast and in-line interferometric channels at two wavelengths, i.e., 635 nm and 488 nm, respectively. At 635 nm, the in-line signal vanishes and the PC signal is maximized, while at 488 nm, the two signals share comparable amplitudes. Two-dimensional scans are shown in FIGS. 5a-5d for both the in-line and phase contrast channels. In FIGS. 5a and 5b, the wavelength is at the center of the stop-band and the active quadrature is the phase contrast channel. In FIGS. 5c and 5d, the wavelength is at 488 nm in the side band and both the phase-contrast and the in-line channels are active.

Optoelectronic semiconductors, such as GaAs on AlGaAs Bragg mirrors, are useful as asymmetric Fabry-Perot (ASFP) electroabsorption modulators, particularly as the contrast of these modulators can be large because of the reflection null that can be achieved by balancing the reflected intensities from the top and bottom interfaces of the GaAs layer by relying on a pi phase shift between the two interfaces [see for example, D. S. Gerber, R. Droopad, and G. N. Maracas, "A GaAs/AlGaAs Asymmetric Fabry-Perot Reflection Modulator with very High Contrast Ratio," IEEE Phot. Tech. Lett., vol. 5, pp. 55, 1993; M. Whitehead and G. Parry, "High-contrast reflection modulation at normal incidence in asymmetric multiple quantum well Fabry-Perot structure," Electron. Lett., vol. 25, pp. 566-568, 1989; R.-H. Yan, R. J. Simes, and L. A. Coldren, "Analysis and design of surface-normal Fabry-Perot electrooptic modulators," IEEE Quant. Electron., vol. 25, pp. 2272, 1989; J. F. Heffernan, M. H. Moloney, J. Hegarty, J. S. Roberts, and M. Whitehead, "All optical high contrast absorptive modulation in an asymmetric Fabry-Perot etalon," Appl. Phys. Lett., vol. 58, pp. 2877, 1991; and A. Larsson and J. Maserjian, "Optically addressed asymmetric Fabry-Perot modulator," Appl. Phys. Lett., vol. 59, pp. 3099, 1991]. These structures are also useful for enhancing diffraction efficiencies during four wave mixing [see for example, D. D. Nolte and K. M. Kwolek, "Diffraction from a Short-Cavity Fabry-Perot: Applications to Photorefractive Quantum Wells," Opt. Commun., vol. 115, pp. 606-616, 1995; K. M. Kwolek, M. R. Melloch, and D. D. Nolte, "Dynamic holography in a reflection/transmission photorefractive quantum-well asymmetric Fabry-Perot," Appl. Phys. Lett., vol. 65, pp. 385, 1994; D. D. Nolte, "Dynamic Holographic Phase Gratings in Multiple Quantum Well Asymmetric Reflection Fabry-Perot Modulators," Opt. Lett., vol. 19, pp. 819-821, 1994; and K. M. Kwolek, M. R. Melloch, D. D. Nolte, and G. A. Brost, "Diffractive Quantum-Well Asymmetric Fabry-Perot: Transverse-Field Photorefractive Geometry," Appl. Phys. Lett., vol. 67, pp. 736, 1995].

Figure 6:
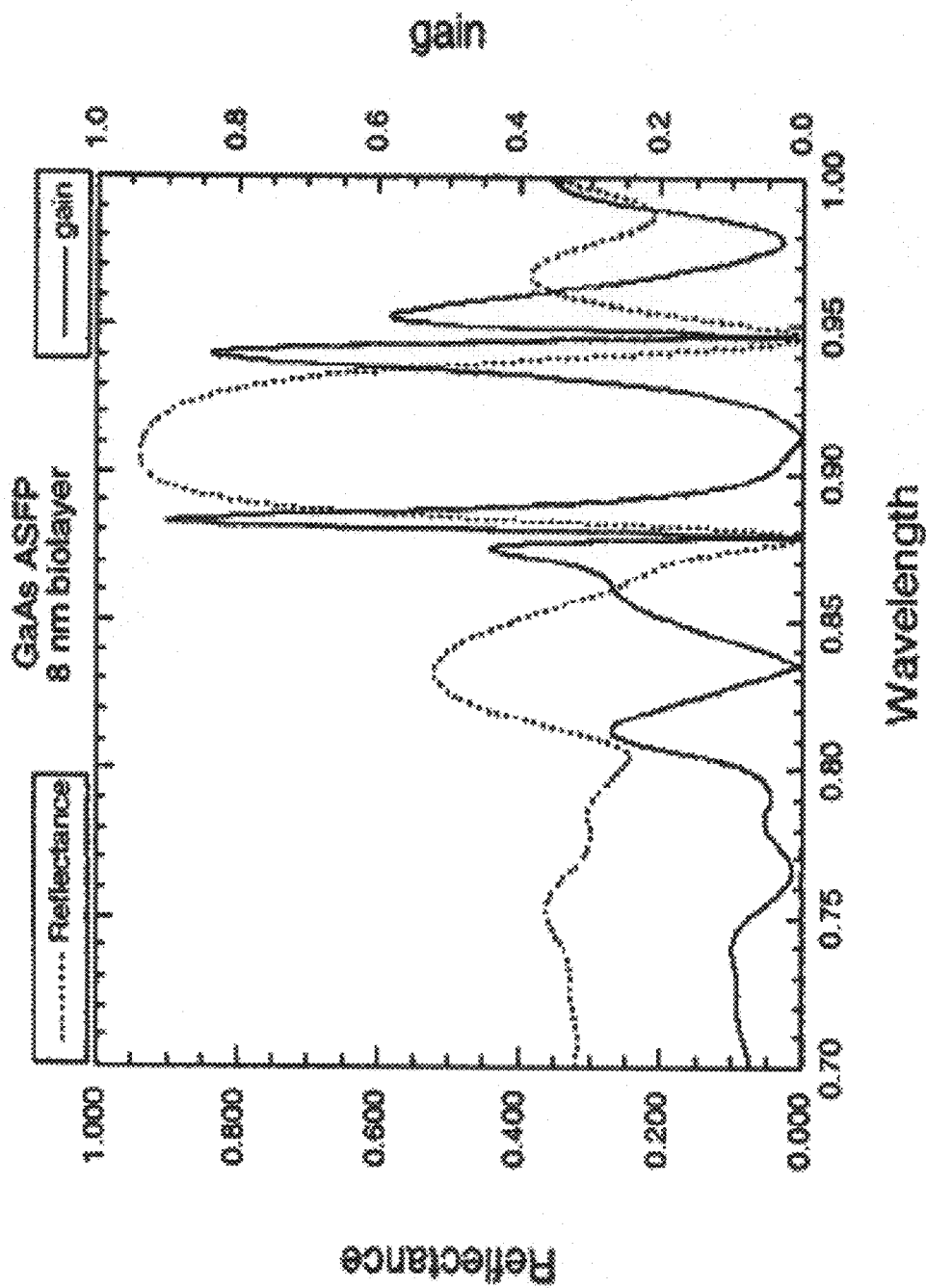
FIG. 6 depicts a graphical representation of reflectance and magnitude gain for a GaAs ASFP structure.

The calculated reflectance of an exemplary GaAs ASFP structure is shown in FIG. 6, along with the magnitude of the interferometric gain (times reflectance, and the gain oscillates in sign as a function of wavelength) in response to a single monolayer of a biofilm with a refractive index of n=1.35. The ASFP structure starting from the top is 950 nm of GaAs on top of a 10× Bragg stack with 72.9 nm of AlAs and 61.1 nm of GaAs. The ASFP null is at 880 nm on the long-wavelength side of the GaAs-layer exciton, and the point of maximum slope (quadrature) is redshifted to 885 nm. The change in reflectance at quadrature is linear in the thickness of the biolayer, with nearly a 2% change for 1 monolayer and an interferometric gain approaching 90%.

Exemplary half-cavity photonic structures of the present invention typically produce gain coefficients times reflectance of less than about 1. As such, their performance is similar to that of a two-wave (two-port) interferometer. In further exemplary embodiments, however, the gain coefficient may be increased by placing the biolayers inside a cavity. According to an illustrated embodiment, two dielectric stacks are separated with about 5-10 micron posts and a sample or serum with target antigens is flowed through the gap between the dielectric mirrors. The slope of the intensity-wavelength curve at quadrature (at the edges of each cavity resonance) becomes much steeper, with much larger corresponding gain coefficients. While this approach may have a reduced wavelength bandwidth and tight constraints on the uniformity of the gap between the dielectric stacks, such a reduction can be addressed by using photolithographically patterned posts composed of photoresist.

Figure 7:
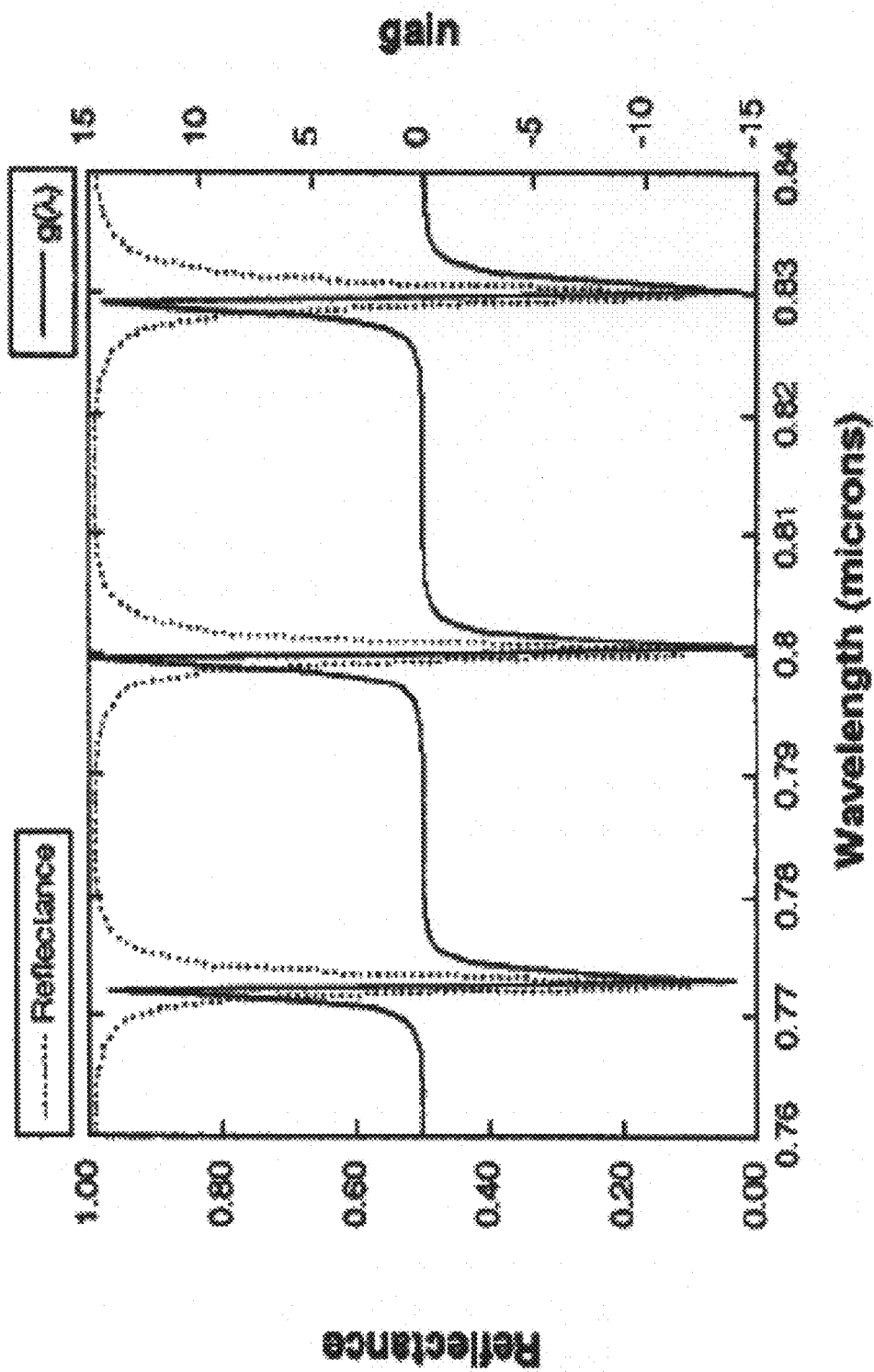
FIG. 7 depicts a graphical representation of reflectance and magnitude gain for a Fabry-Perot cavity with a 10 micron air gap between 3× MgF/TiO$_2$ stacks centered at 800 nm.

The calculated interferometric gain times reflectance in response to a monolayer biofilm and the reflectance of an exemplary Fabry-Perot structure composed of two 3× MgF/SiO$_2$ stacks centered at 800 nm, one inverted over the other with a 10 micron air gap, is shown in FIG. 7. The gain is calculated for 1 mL biolayer on one stack surface, and the free-spectral range of the Fabry-Perot cavity is about 30 nm, while the bandwidth is about 1 nm. Each cavity resonance has two quadratures in opposite quadrants that flip the sign of the gain as the wavelength tunes through resonance.

The maximum gain times reflectance in the illustrated device is approximately 15, which is over an order of magnitude larger than achieved with an ideal Mach-Zender or the self-referencing half-cavities described above. However, the bandwidth is smaller than dielectric stack or asymmetric Fabry-Perot structures. The gain-bandwidth product of the exemplary resonant cavity shown in FIG. 7 is about 15 nm/ML, while the product for the half-cavity dielectric stack in FIG. 3 is about 50 nm/ML. It should be understood that bandwidth is important for situations when laser tunability or wavelength stability are an issue, or when the resonant wavelength varies across the disk in the resonant case. However, if the bandwidth is engineered to a small value, then the gain-bandwidth product is not the relevant figure-of-merit, and the gain alone is important for determining device S/N and sensitivity.

Figure 8:
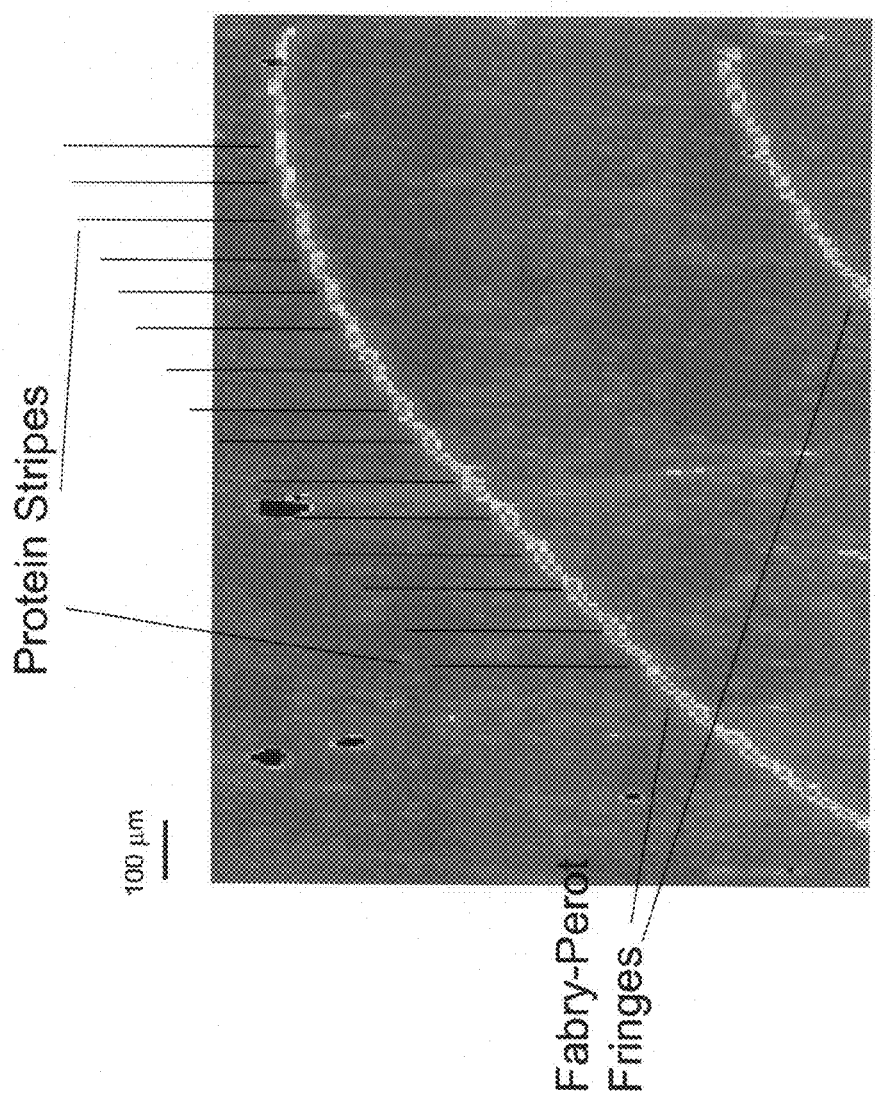
FIG. 8 depicts Fabry-Perot fringes in an exemplary resonant cavity constructed of two mirrors optimized at 635 nm and wherein protein stripes printed on one of the mirrors is detected as a spatial modulation of the Fabry-Perot fringes.

An experimental demonstration of protein detection within a Fabry-Perot cavity is shown in FIG. 8 for a cavity constructed of two 635 mirrors that face each other across a 10 micron gap. Printed on the surface of one of the mirrors is a protein stripe pattern. The bright arcs in FIG. 8 are the resonant Fabry-Perot fringes. The arcs show a periodic undulation that matches the protein stripe pattern, showing that the fringe location is affected by the presence of the printed protein pattern inside the cavity.

While exemplary embodiments incorporating the principles of the present teachings have been disclosed hereinabove, the present teachings are not limited to the disclosed embodiments. Instead, this application is intended to cover any variations, uses, or adaptations of the invention using its general principles. Further, this application is intended to cover such departures from the present disclosure as come within known or customary practice in the art to which this invention pertains.

What is claimed is:

1. A detection system for detecting target material comprising:
   a photonic structure having a reflectance-band and associated side bands;
   an illumination source for illuminating at a wavelength in at least one of an edge of the reflectance-band and the side bands of the photonic structure and for generating a return beam;
   a detector system having an intensity-sensitive channel configured to detect an in-line signal from the return beam and a phase-sensitive channel configured to detect a differential phase contrast signal from the return beam; and
   a processing system for receiving and adding in quadrature the in-line signal and the differential phase contrast signal to generate a joint signal, and for determining one of the presence or the absence of the target material on the photonic structure using the joint signal.

2. The detection system of claim 1, wherein the joint signal is the sum of the squares of the in-line signal and the differential phase contrast signal.

3. The detection system of claim 1, wherein the photonic structure is immobilized on a biological compact disk.

4. The detection system of claim 3, further comprising:
   a spin motor upon which the biological compact disk can be mounted, the spin motor being configured to rotate the biological compact disk.

5. The detection system of claim 4, further comprising:
   a linear stage for translating the biological compact disk relative to the illumination source;
   wherein the rotation of the biological compact disk by the spin motor and the translation of the biological compact disk relative to the illumination source by the linear stage creates a polar coordinate system that can be used for referencing any point on the biological compact disk.

6. The detection system of claim 1, wherein the detector system includes a segmented photodetector configured to simultaneously measure differential phase and in-line intensity of a response modulus.

7. The detection system of claim 6, wherein the segmented photodetector is configured to detect the response modulus by separately detecting the in-line signal and the differential phase contrast signal.

8. A method for detecting the presence of an antigen on a photonic structure, the method comprising:
   exposing the photonic structure to a sample that may contain the antigen, the photonic structure having a reflectance-band and side bands;
   illuminating at a wavelength in at least one of an edge of the reflectance-band and the side bands of the photonic structure with an illumination source to create a return beam;
   detecting the return beam with a detector system having an intensity-sensitive detection function and a phase-sensitive detection function;
   detecting an in-line quadrature signal from the return beam using the intensity-sensitive detection function of the detector system;
   detecting a differential phase contrast quadrature signal from the return beam using the phase-sensitive detection function of the detector system;

receiving the in-line quadrature signal and the differential phase contrast quadrature signal;

combining the in-line quadrature signal and the differential phase contrast quadrature signal to generate a joint signal, and determining one of the presence or the absence of the target material on the photonic structure using the joint signal.

9. The method of claim 8, wherein the combining step includes taking the sum of the squares of the in-line quadrature signal and the differential phase contrast quadrature signal to form the joint signal.

10. The method of claim 8, wherein the detecting step includes:

determining a detection wavelength in the side bands, the detection wavelength having approximately the maximum gain; and detecting the in-line quadrature signal and the differential phase contrast quadrature signal at the detection wavelength.

\* \* \* \* \*